US012622712B2

(12) United States Patent
Kugler

(10) Patent No.: US 12,622,712 B2
(45) Date of Patent: May 12, 2026

(54) DEVICES, SYSTEMS AND METHODS FOR IMPROVING SUCTION IN MEDICAL PROCEDURES

(71) Applicant: Seigla Holdings Limited, Dublin (IE)

(72) Inventor: Chad J. Kugler, Buffalo, MN (US)

(73) Assignee: Seigla Holdings Limited, Dublin (IE)

( * ) Notice: Subject to any disclaimer, the term of this patent is extended or adjusted under 35 U.S.C. 154(b) by 839 days.

(21) Appl. No.: 17/942,721

(22) Filed: Sep. 12, 2022

(65) Prior Publication Data

US 2023/0077997 A1 Mar. 16, 2023

Related U.S. Application Data

(60) Provisional application No. 63/242,875, filed on Sep. 10, 2021.

(51) Int. Cl.
| | |
|---|---|
| *A61B 17/22* | (2006.01) |
| *A61B 17/135* | (2006.01) |
| *A61B 90/40* | (2016.01) |
| *A61G 10/02* | (2006.01) |
| *A61B 17/00* | (2006.01) |

(52) U.S. Cl.
CPC ............ *A61B 17/22* (2013.01); *A61B 17/135* (2013.01); *A61B 90/40* (2016.02); *A61G 10/023* (2013.01); *A61B 2017/00557* (2013.01); *A61B 2017/22079* (2013.01); *A61B 2217/005* (2013.01)

(58) Field of Classification Search
CPC .......... A61B 17/320725; A61B 17/135; A61B 17/22; A61B 90/40; A61B 2017/00557; A61B 2017/22079; A61B 2217/005; A61B 2017/2215; A61B 17/32037; A61G 10/023
See application file for complete search history.

(56) References Cited

U.S. PATENT DOCUMENTS

| | | | | |
|---|---|---|---|---|
| 3,303,841 A | * | 2/1967 | Clarence | .............. A61H 9/0071 |
| | | | | 600/16 |
| 4,664,651 A | * | 5/1987 | Weinshenker | ... A61B 5/150099 |
| | | | | 600/490 |
| 5,234,403 A | | 8/1993 | Yoda et al. | |
| 5,334,211 A | * | 8/1994 | Shiber | .................. A61B 18/245 |
| | | | | 606/159 |
| 5,514,155 A | * | 5/1996 | Daneshvar | ......... A61B 17/1325 |
| | | | | 602/53 |
| 5,569,204 A | | 10/1996 | Cramer | |

(Continued)

FOREIGN PATENT DOCUMENTS

| | | | | |
|---|---|---|---|---|
| WO | WO-0202181 A1 | * | 1/2002 | ....... A61B 17/12118 |

*Primary Examiner* — Wesley G Harris
(74) *Attorney, Agent, or Firm* — Christensen, Fonder, Dardi & Herbert PLLC; John P. Fonder

(57) ABSTRACT

Systems and methods for removing material from a blood vessel or cavity inside a body by suction, wherein the magnitude of suction is increased by applying extracorporeal positive pressure. Positive pressure outside the body is increased such that the potential negative pressure inside the body may be increased. Methods include inserting a catheter into a blood vessel or cavity and positioning a distal opening of the catheter proximate the material to be removed. Extracorporeal positive pressure is applied to at least a portion of the body containing the material to be removed, and suction is simultaneously applied to the catheter to more effectively remove the material.

8 Claims, 16 Drawing Sheets

(56)  References Cited

U.S. PATENT DOCUMENTS

| | | | |
|---|---|---|---|
| 5,749,858 A | | 5/1998 | Cramer |
| 5,827,229 A | | 10/1998 | Auth et al. |
| 5,938,645 A | | 8/1999 | Gordon |
| 6,231,507 B1 * | | 5/2001 | Zikorus ................ A61B 17/135 |
| | | | 600/437 |
| 6,849,068 B1 | | 2/2005 | Bagaoisan et al. |
| 7,224,250 B2 | | 5/2007 | Nemoto et al. |
| 7,250,042 B2 | | 7/2007 | Kataishi et al. |
| 7,736,355 B2 | | 6/2010 | Itou et al. |
| 7,896,825 B2 | | 3/2011 | Atkinson et al. |
| 8,764,724 B2 | | 7/2014 | Itou et al. |
| 9,017,309 B2 | | 4/2015 | Tanikawa et al. |
| 10,390,849 B2 | | 8/2019 | Kugler et al. |
| 10,485,551 B2 | | 11/2019 | Turjman et al. |
| 10,485,564 B2 | | 11/2019 | Goyal |
| 10,799,244 B2 | | 10/2020 | Cully et al. |
| 10,806,474 B2 | | 10/2020 | Kugler et al. |
| 10,863,999 B2 | | 12/2020 | Wallace et al. |
| 2003/0069528 A1 * | | 4/2003 | Herz .................... A61H 9/0007 |
| | | | 601/152 |
| 2005/0087573 A1 * | | 4/2005 | Unsworth ............ A47G 25/904 |
| | | | 223/112 |
| 2012/0022422 A1 * | | 1/2012 | Ravikumar .......... A61B 17/135 |
| | | | 602/62 |
| 2013/0317538 A1 * | | 11/2013 | Perry ............... A61B 5/150068 |
| | | | 606/202 |
| 2017/0215890 A1 * | | 8/2017 | Turjman .......... A61B 17/12109 |

* cited by examiner 1C
1B
FIG. 1A
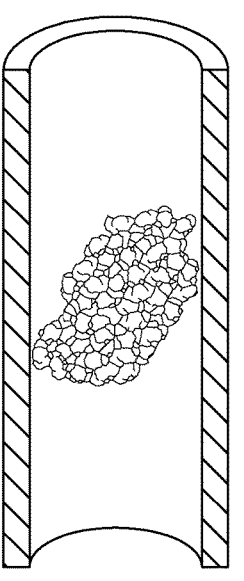
FIG. 1C
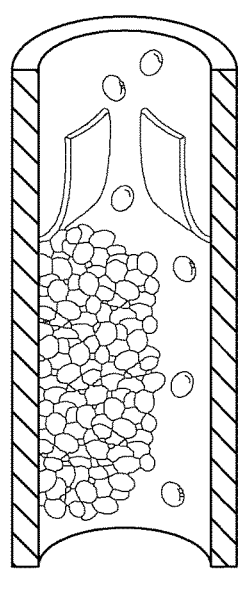
FIG. 1B

INFLATION
FLUID
SOURCE

DEVICES, SYSTEMS AND METHODS FOR IMPROVING SUCTION IN MEDICAL PROCEDURES

CROSS-REFERENCE TO RELATED APPLICATIONS

The present application claims the benefit of U.S. Provisional Application No. 63/242,875, filed Sep. 10, 2021, the disclosures of which are incorporated by reference herein

FIELD

The present disclosure generally relates to devices, systems and methods for providing intracorporeal suction to remove material from the body, with utility to, for example, removing blood clots from blood vessels to restore blood flow.

BACKGROUND

Many medical procedures use suction to remove material from inside the body. For example, a blood clot may be removed from a blood vessel to restore blood flow by applying suction via a catheter disposed in the blood vessel proximate the blood clot. In this case, the efficiency of clot removal by suction is limited by several factors including the magnitude of suction (i.e., negative pressure or vacuum), catheter characteristics, clot composition and morphology, and clot location. While it may not be possible to change the clot composition, morphology or location, improvements have been made to catheter designs to increase the proficiency of clot removal. In addition, improvements have been made to suction pump designs to increase the magnitude of suction. However, such improvements are limited by atmospheric or ambient pressure which, under normal circumstances, is about 1 ATM (14.7 PSI or 760 mmHg), and thus a perfect vacuum is limited to about −1 ATM (−14.7 PSI or −760 mmHg). There is an ongoing need to improve material removal systems to address challenging clinical conditions that limit their efficacy.

SUMMARY

The present disclosure describes various devices, systems and methods for improving suction magnitude used in medical procedures. In one general embodiment, positive pressure outside the body is increased such that the potential negative pressure inside the body may be increased. Positive pressure outside the body may be increased by selectively applying compression, for example. By way of illustration, if X ATM of positive compression is applied outside the body, the potential negative pressure or vacuum inside the body may increase to −(1 +X) ATM, and thus the magnitude of suction may be proportionately increased.

As used herein, positive pressure or compression outside the body may be referred to as extracorporeal positive pressure or compression, and the actual or potential negative pressure or vacuum inside the body may be referred to as intracorporeal potential negative pressure or vacuum.

Extracorporeal compression may be applied in a variety of ways in terms of means, magnitude, location, time and sequence. For example, extracorporeal compression may be applied systemically (e.g., around the whole body) or locally (e.g., at or around the location of the material to be removed). Extracorporeal compression may be applied continuously, intermittently, simultaneously, sequentially or alternatively at multiple locations, for example. Extracorporeal compression may be applied mechanically or pneumatically, for example.

The embodiments described herein may be applied to a number of diseases that occur when obstructive material such as thrombus collects in blood vessels. Deep vein thrombosis (DVT), for example, occurs when blood clots and/or thrombus collect in the blood veins of the legs. If DVT is left untreated, blood clots can break free and travel through the bloodstream toward the heart. These blood clots can lodge in the blood vessels of a lung, blocking blood flow and causing a pulmonary embolism.

An example embodiment provides a method of removing material from a blood vessel or cavity inside a body. A catheter may be inserted into the blood vessel or cavity, wherein the catheter includes an elongate shaft, a proximal portion, a distal portion and a lumen extending therethrough to a distal opening. The distal opening of the catheter may be positioned in the blood vessel or cavity proximate the material to be removed. Extracorporeal positive pressure may be applied to at least a portion of the body containing the material to be removed. Suction may be applied to the proximal portion of the catheter while the extracorporeal positive pressure is being applied. The suction may be applied before applying extracorporeal positive pressure, and the suction may continue while the extracorporeal positive pressure is being applied.

The catheter may be inserted into the body at an access site, wherein the access site is proximal of the portion of the body where extracorporeal pressure is applied. The extracorporeal positive pressure may be applied at a location that surrounds the portion of the body containing the material to be removed, and/or at locations that are proximal and distal of the portion of the body containing the material to be removed.

The extracorporeal positive pressure may be applied by a pressure chamber surrounding the entire body, or a pressure chamber surrounding less than the entire body, such as an upper torso or a limb. Alternatively, the extracorporeal positive pressure may be applied by a compression device that applies static pressure such as an elastic compression sock or sleeve, an inflatable device, or a combination thereof. As a further alternative, extracorporeal compression may be applied by a compression device that applies dynamic pressure, such as a multicompartment inflatable boot or sleeve and associated pump with controls that dynamic pressure progressively in a distal to proximal direction.

Another example embodiment provides a method of removing a blood clot from a peripheral blood vessel in a limb by inserting a catheter into the blood vessel via an access site proximal of the blood clot, positioning a distal opening of the catheter in the blood vessel proximate the blood clot to be removed, applying extracorporeal positive pressure around a portion of the limb distal of the access site and distal of the material to be removed, and applying suction to the proximal portion of the catheter while the extracorporeal positive pressure is being applied.

Yet another embodiment provides a method of removing a cerebrovascular blood clot by positioning the patient's head in a pressure chamber, inserting a catheter into the appropriate blood vessel via an access site proximal of the blood clot, positioning a distal opening of the catheter in the blood vessel proximate the blood clot to be removed, increasing a pressure in the pressure chamber to a value above atmospheric pressure, applying suction to the proximal portion of the catheter while the extracorporeal positive pressure is being applied.

In another example embodiment, the present disclosure provides a method for removing obstructive material (e.g., clot, thrombus, stones, discharge, etc.) from a blood vessel or cavity of a body by positioning a covering to enclose (optionally with a sealed perimeter) at least a portion of the body. An interior space defined by the covering and the seal may be placed in fluid communication with a positive (positive) pressure source so that positive pressure is applied to the portion of the body enclosed by the covering. A catheter may be provided having a proximal end/opening, a distal end/opening, and a tubular shaft extending therebetween defining a lumen extending therethrough. The distal opening of the catheter may be positioned near a target location inside the body and the proximal opening of the catheter may be placed in fluid communication with a negative (sub-atmospheric) pressure source (e.g., vacuum) so that negative pressure is applied at the target location near the distal end of the catheter.

In some example applications, the target location is located inside a cerebral vasculature of the body and/or located inside a cranial cavity of the body. In some example applications the target location is located inside a peripheral vasculature of the body and/or located inside a limb of the body (e.g., a leg).

In some example embodiments, the positive pressure may have a magnitude greater than 80 mm Hg (gauge) and less than 120 mm Hg (gauge). In some example embodiments, the positive pressure may have a magnitude greater than 200 mm Hg (gauge) and less than 800 mm Hg (gauge). In some example embodiments, the negative pressure may have a magnitude greater than −760 mm Hg (gauge) and less than −100 mm Hg (gauge). Gauge pressure generally refers to the pressure measured relative to the ambient atmospheric pressure.

In another example embodiment, the present disclosure provides a system for selectively applying positive pressure to a body of a patient including a covering (optionally with a sealed perimeter) configured to enclose a portion of the body, the covering having an inside surface defining an interior space dimensioned and configured to receive a portion of the body. The system may further include a positive pressure source and a valve mechanism operatively coupled between the interior space and the positive pressure source, wherein the valve mechanism selectively applies positive pressure to the portion of the body. In some embodiments, the covering is configured to enclose the head, torso, arms, hands, legs, and/or feet of the body. In some embodiments, the covering comprises a sleeve portion that is dimensioned and configured to encircle an arm of the body. In some embodiments, the covering comprises a leg portion that is dimensioned and configured to encircle a leg of the body. In some embodiments, the covering comprises a torso portion that is dimensioned and configured to encircle a torso of the body. In some embodiments, the covering comprises a headpiece that is dimensioned and configured to encircle a head of the body.

In some embodiments, the positive pressure source comprises a compressor or pump and a reservoir. In some embodiments, the positive pressure source comprises a blower.

The above summary is not intended to describe each and every embodiment or implementation of the present disclosure.

BRIEF DESCRIPTION OF THE DRAWINGS

The accompanying drawings, which are incorporated into and constitute a part of this specification, illustrate various exemplary embodiments and, together with the description, serve to explain the principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements, other than those specifically shown, are contemplated and are within the scope of the present disclosure.

There are many inventions described and illustrated herein. The described inventions are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended reflect or indicate the embodiment(s) is/are "example" embodiment(s).

The drawings illustrate example embodiments of the present disclosure and, along with the description, serve to explain the principles of the disclosure. The drawings are only illustrative of certain embodiments and do not limit the disclosure or invention.

FIG. 1A is a schematic anterior view illustrating a patient's body having a vascular system.

FIG. 1B is a schematic cross-sectional perspective view showing a blood clot located in a peripheral blood vessel such as an artery or vein (as shown).

FIG. 1C is a schematic cross-sectional perspective view showing a blood clot located in a blood vessel in the brain.

Figure 2:
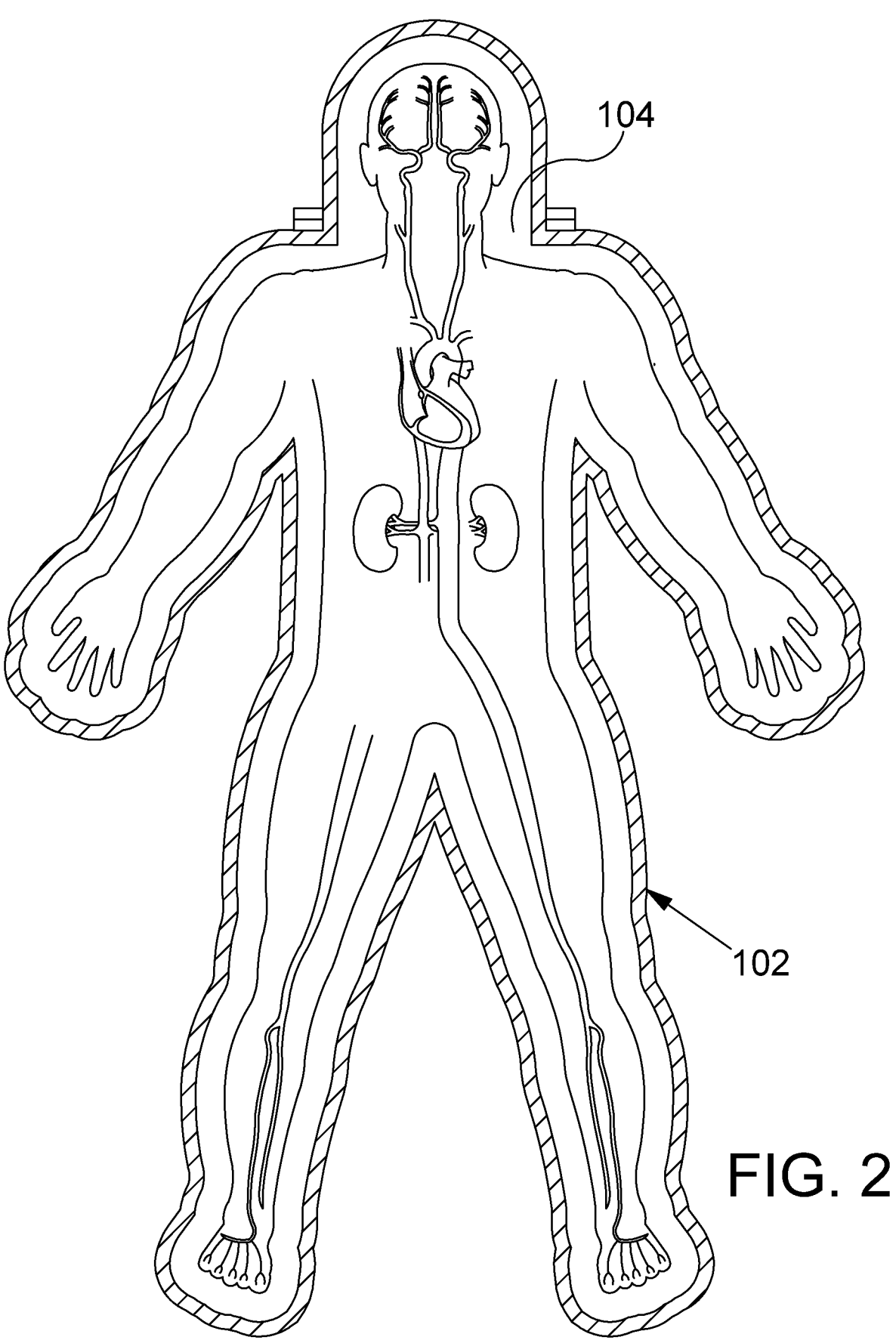

FIG. 2 is a schematic cross-sectional view showing an air-tight covering or chamber disposed about the entire body of a patient.

Figure 3:
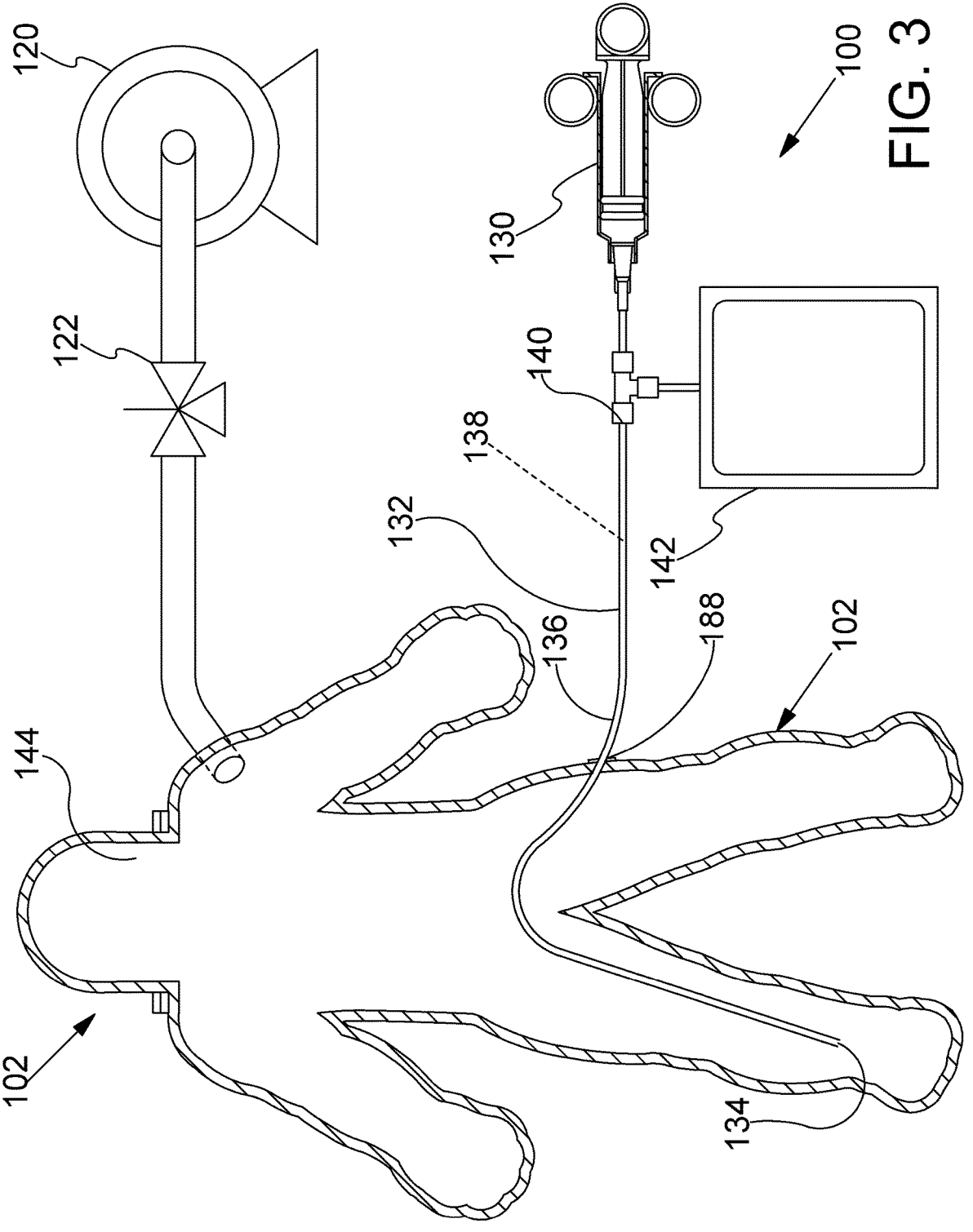

FIG. 3 is schematic plan view showing an example system including a catheter, the covering shown in FIG. 2, and a pump.

Figure 4:
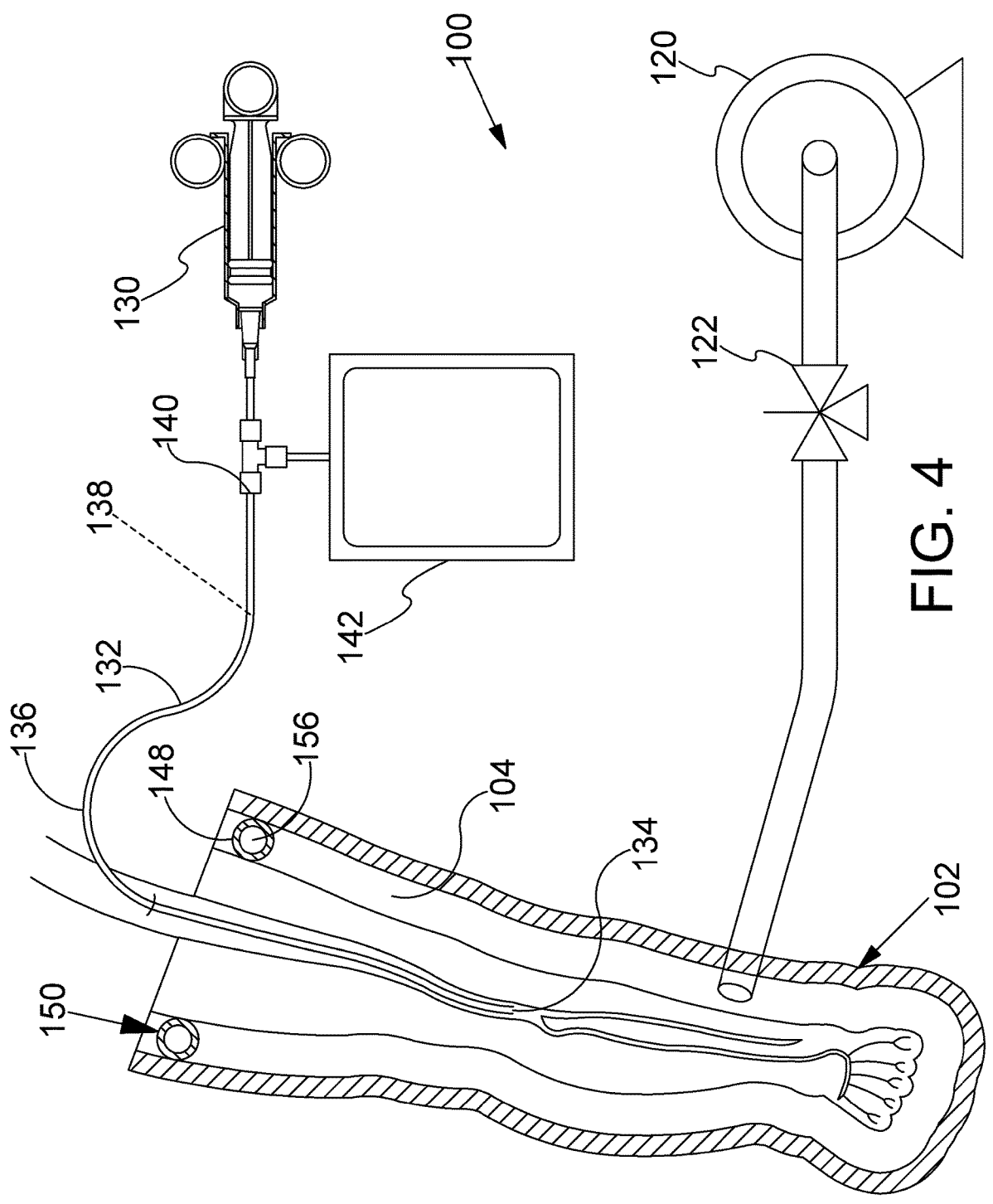

FIG. 4 is schematic plan view showing an example system including a catheter, a covering surrounding a limb, and a pump.

Figure 5:
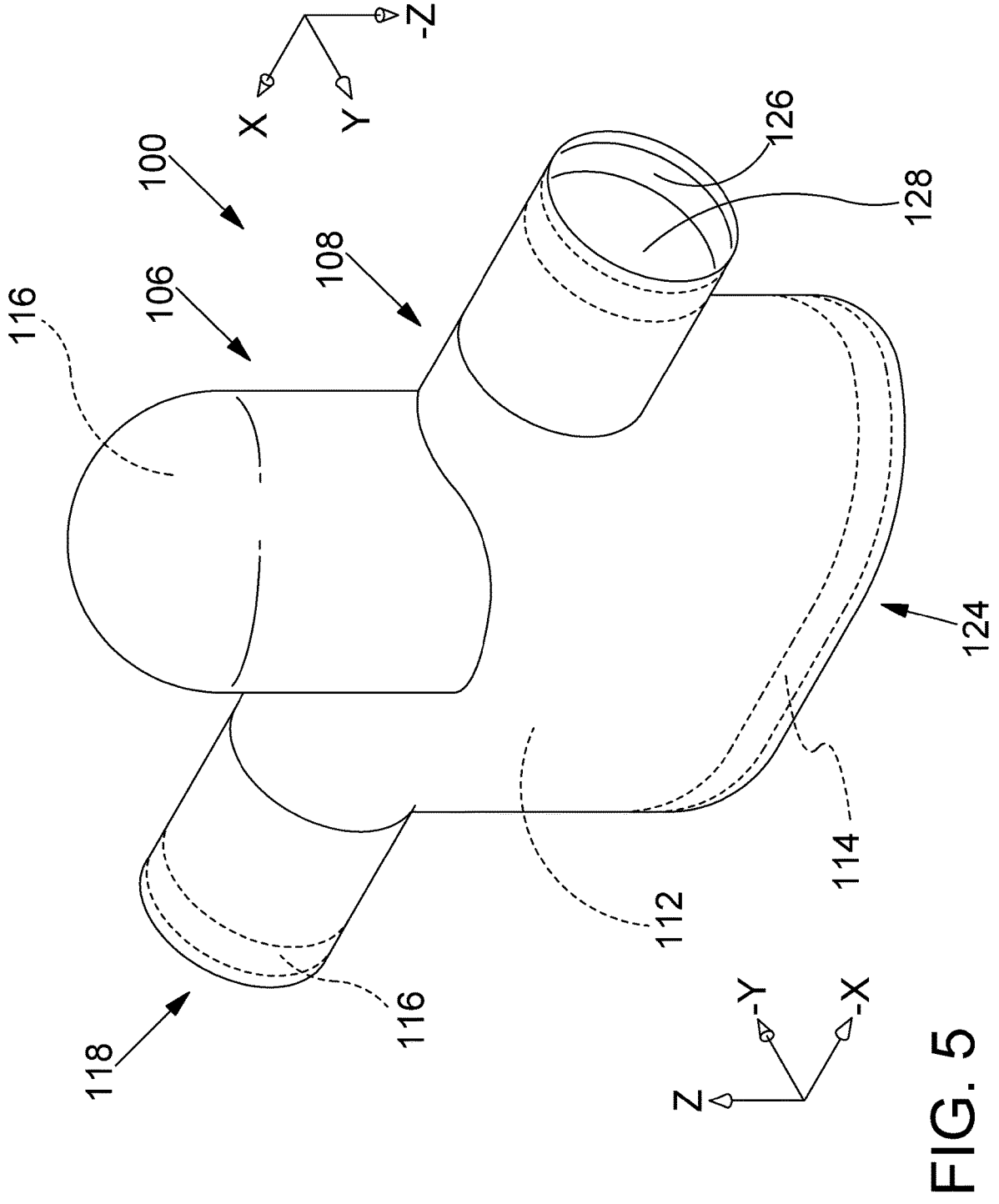

FIG. 5 is perspective view showing an example air-tight covering or chamber for selectively applying positive pressure to the upper torso and head of a patient.

Figure 6:
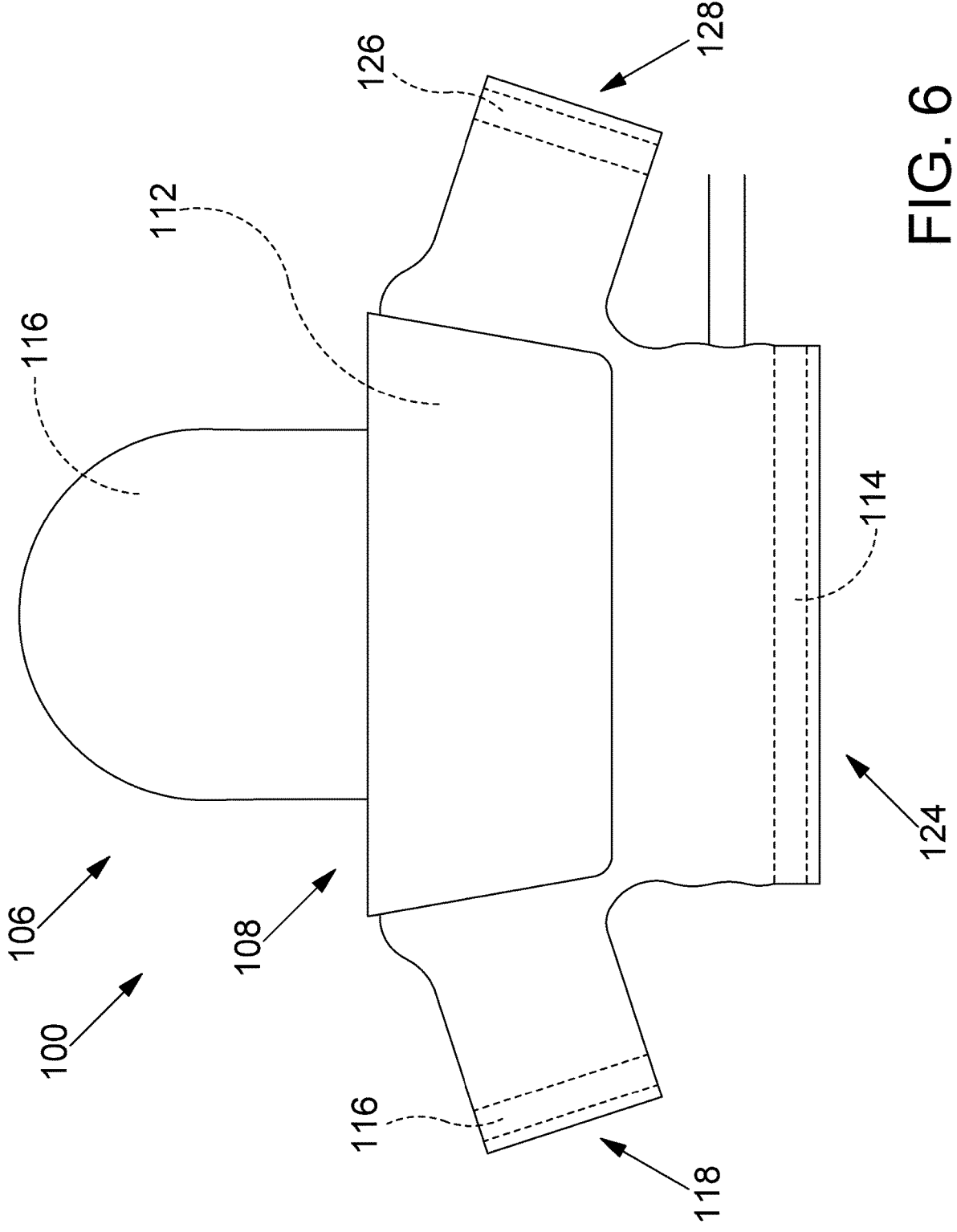

FIG. 6 is an anterior plan view of the covering shown in FIG. 5.

Figure 7:
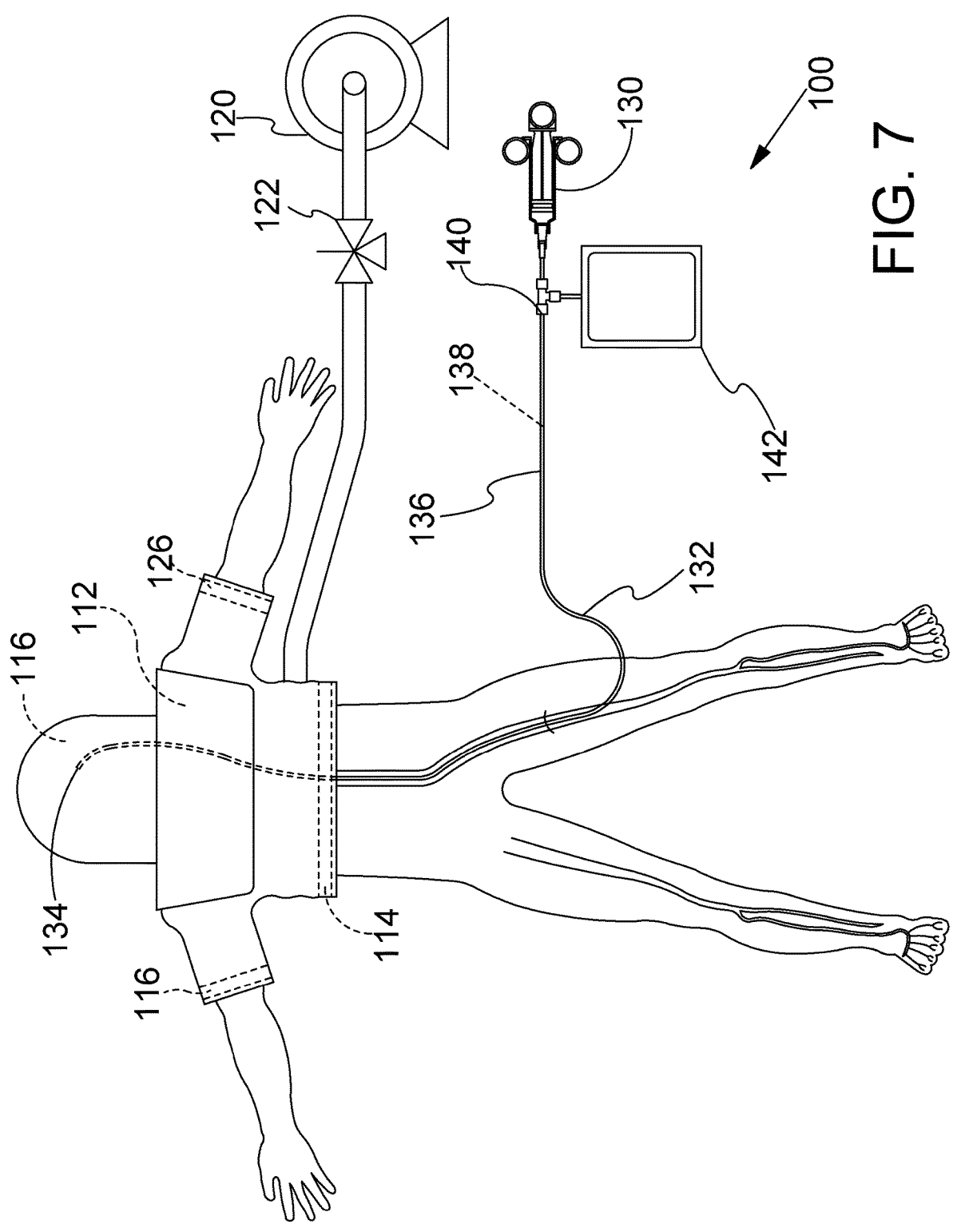

FIG. 7 is schematic plan view showing an example system including a catheter, the covering shown in FIG. 6, and a pump.

Figures 8A, 8B:
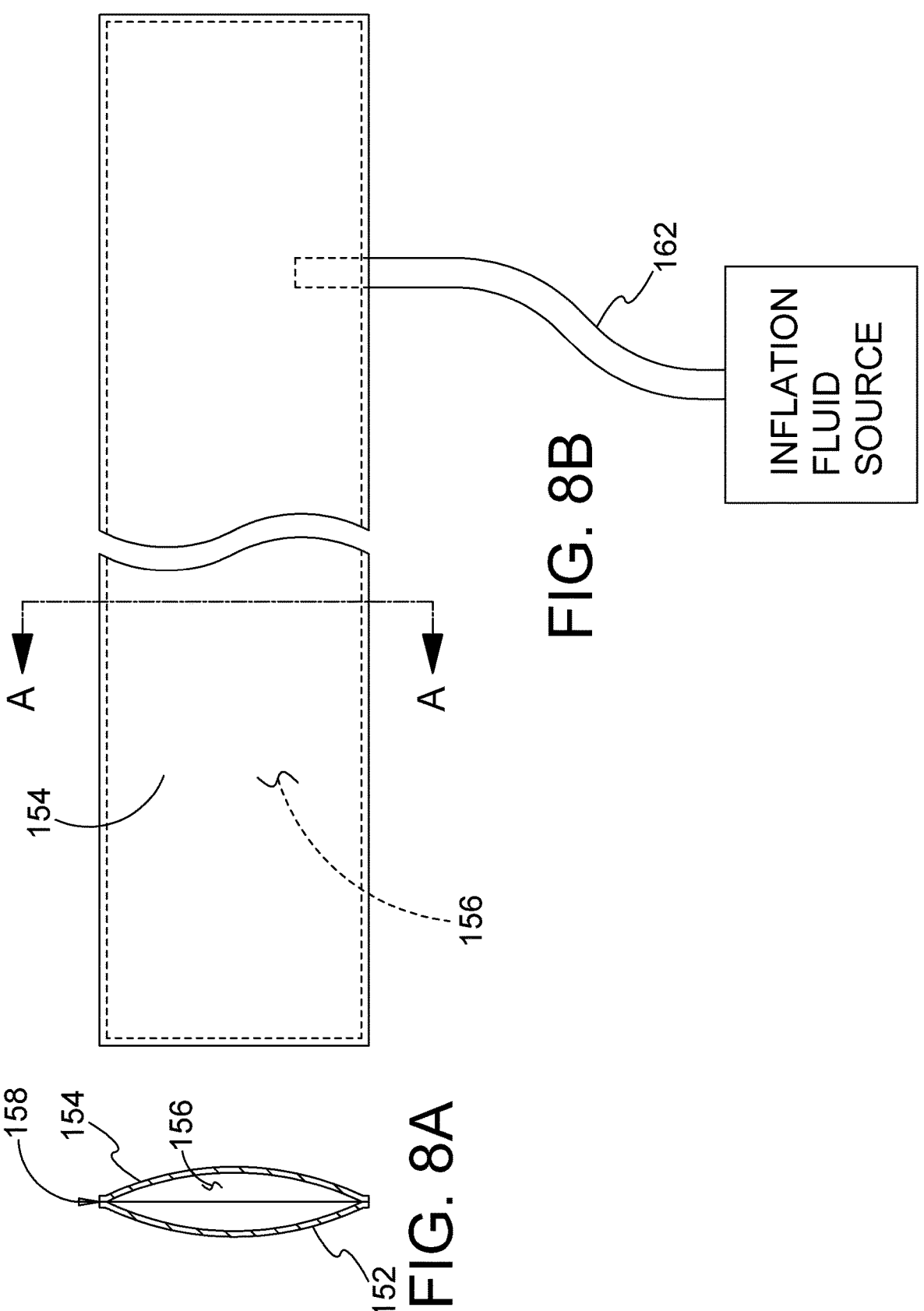

FIG. 8A is a cross-sectional view showing an example sealing member in accordance with the present detailed description.

FIG. 8B is a plan view of the sealing member shown in FIG. 8A.

Figures 9A, 9B:
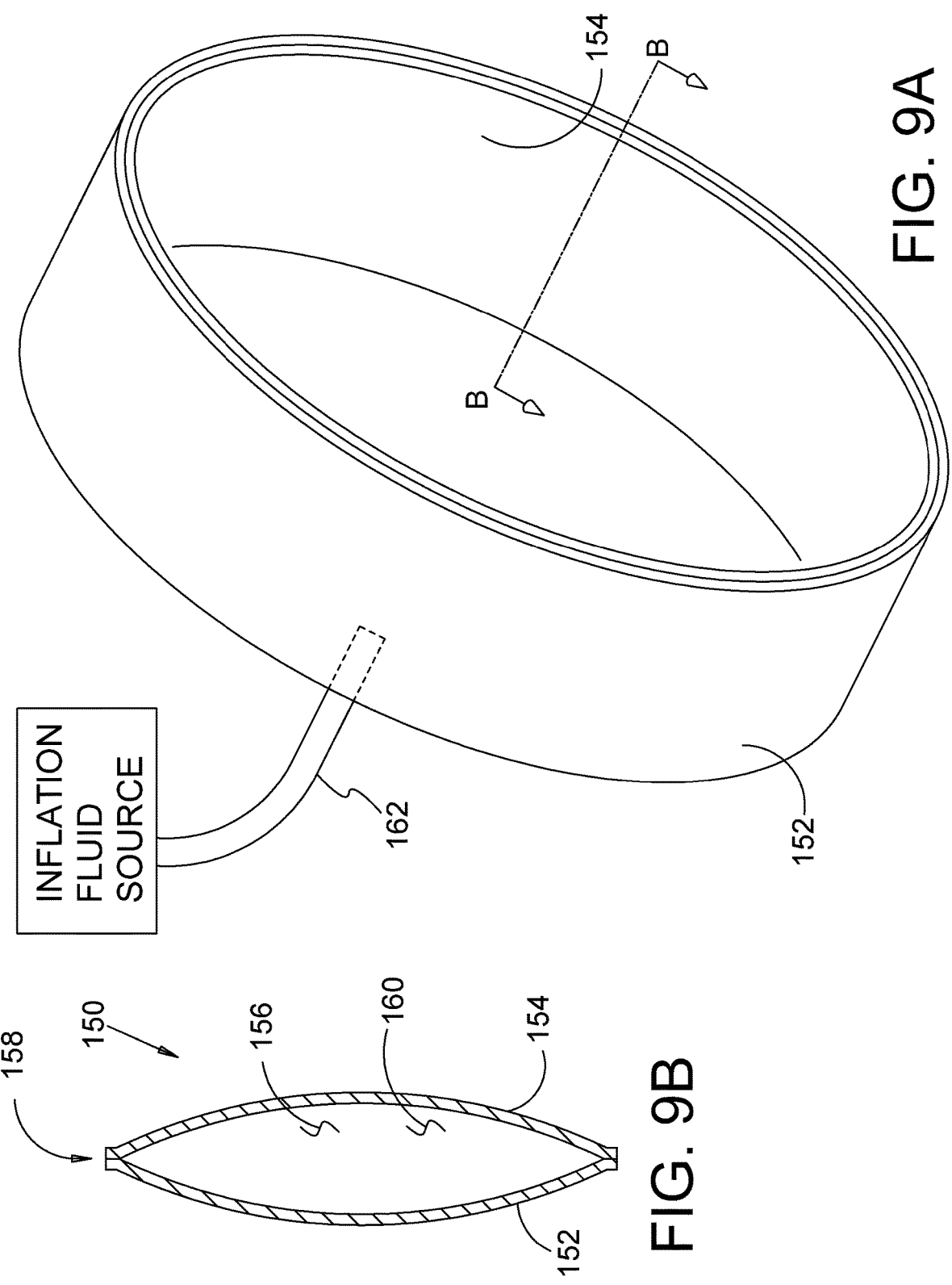

FIG. 9A is a perspective view of a sealing member in accordance with another example embodiment.

FIG. 9B is a cross-sectional view created by the hypothetical cutting of a sealing member along section B-B shown in FIG. 9A.

Figure 10A:
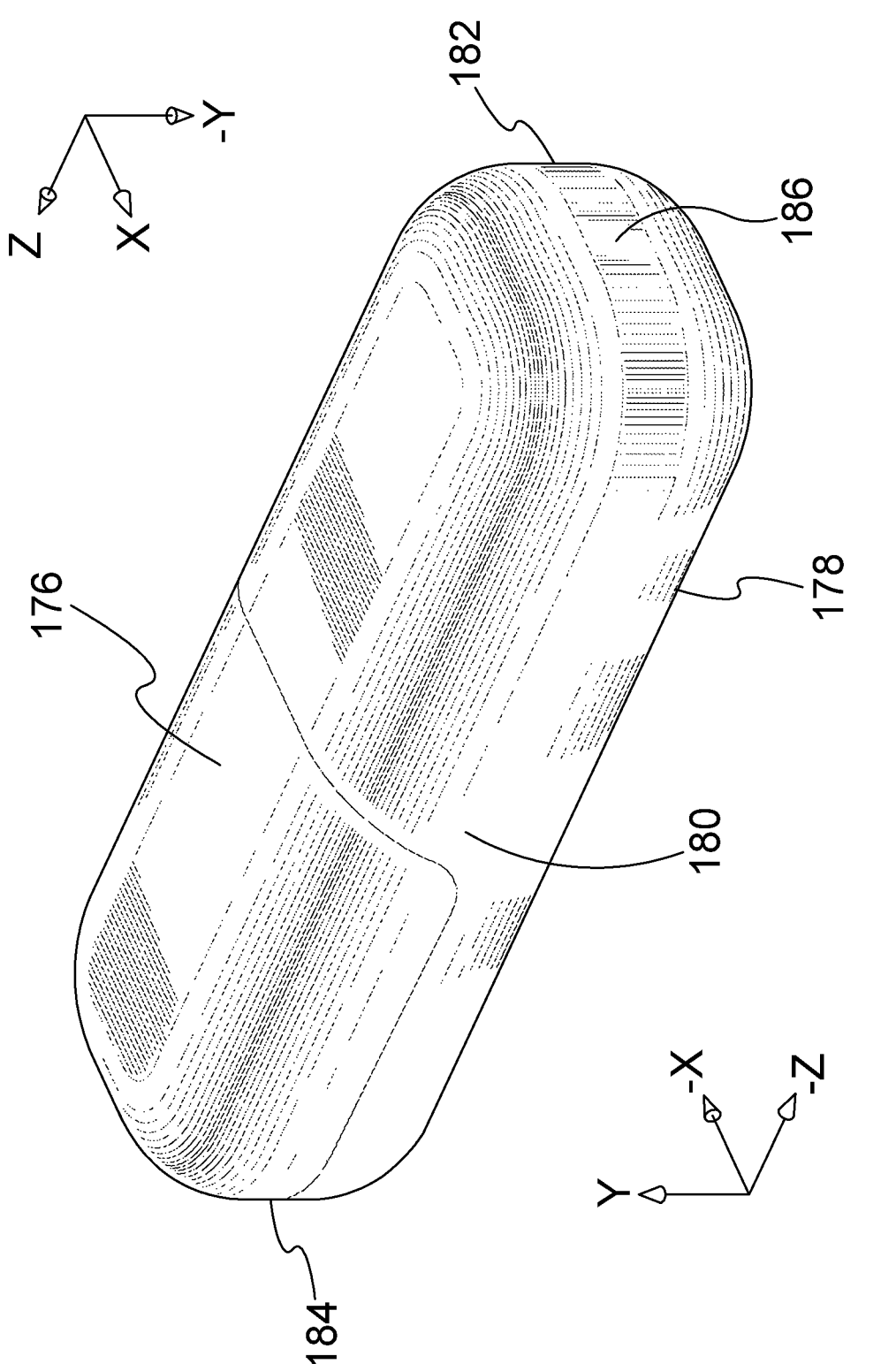

FIG. 10A is a perspective view showing an example air-tight covering or chamber.

Figures 10B, 10C, 10D:
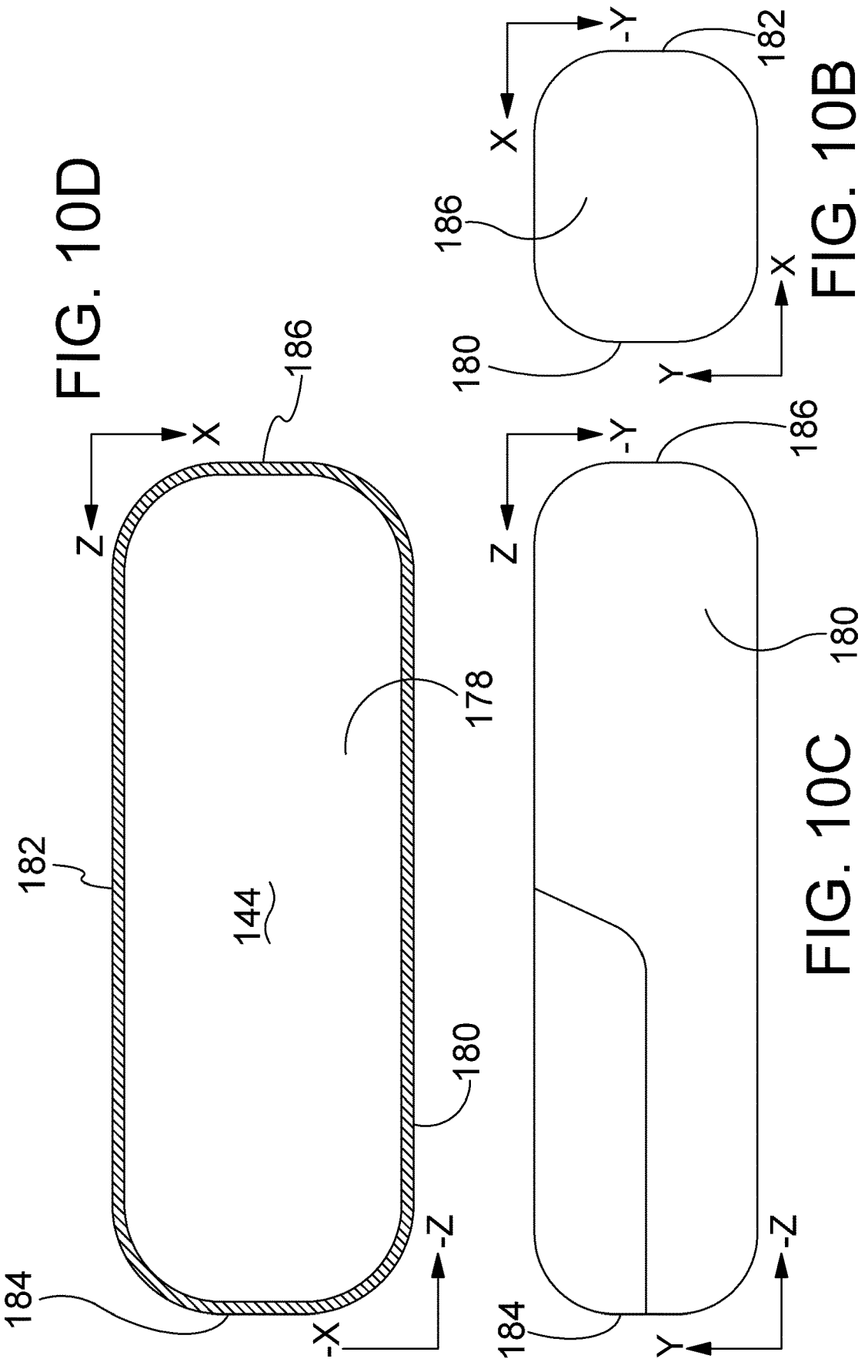

FIG. 10B is a front view of the covering shown in FIG. 10A.

FIG. 10C is a side view of the covering shown in FIG. 10A.

FIG. 10D is a cross-sectional top view of the covering shown in FIG. 10A.

Figure 11:
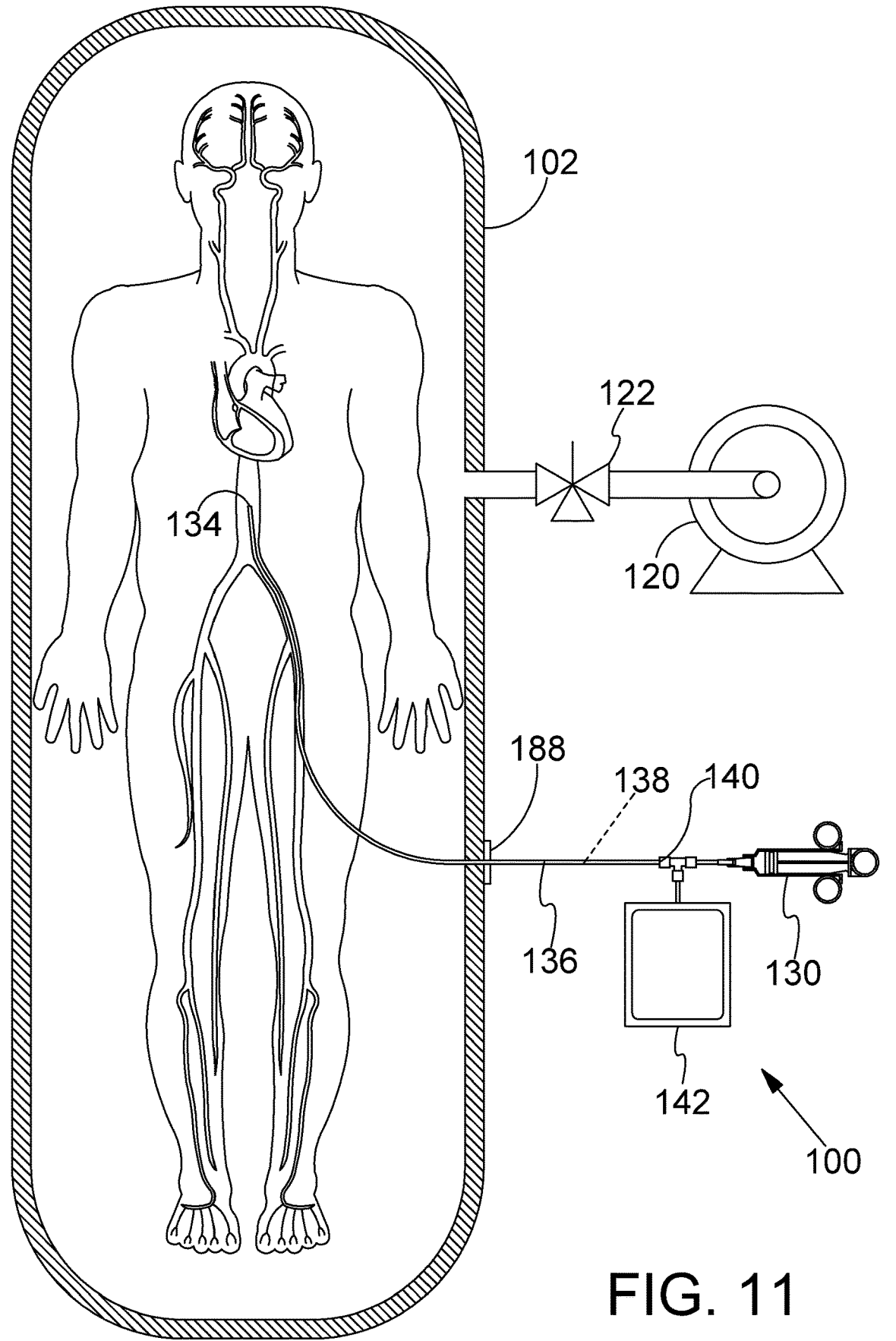

FIG. 11 is schematic plan view showing an example system including a catheter, the covering shown in FIG. 10, and a pump.

Figure 12:
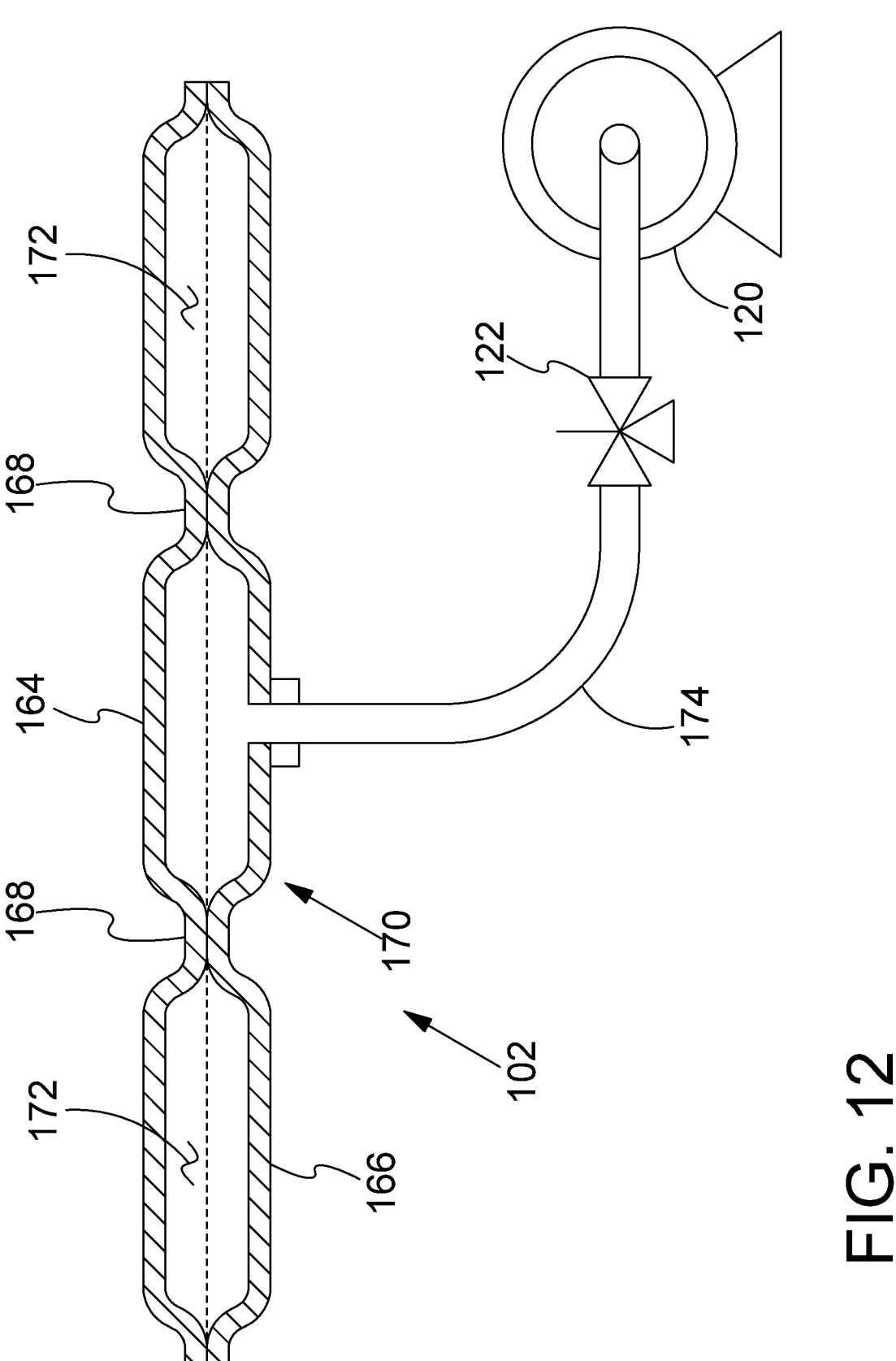

FIG. 12 is a cross-sectional view showing an example system for selectively applying positive pressure to the body of a patient.

Figure 13:
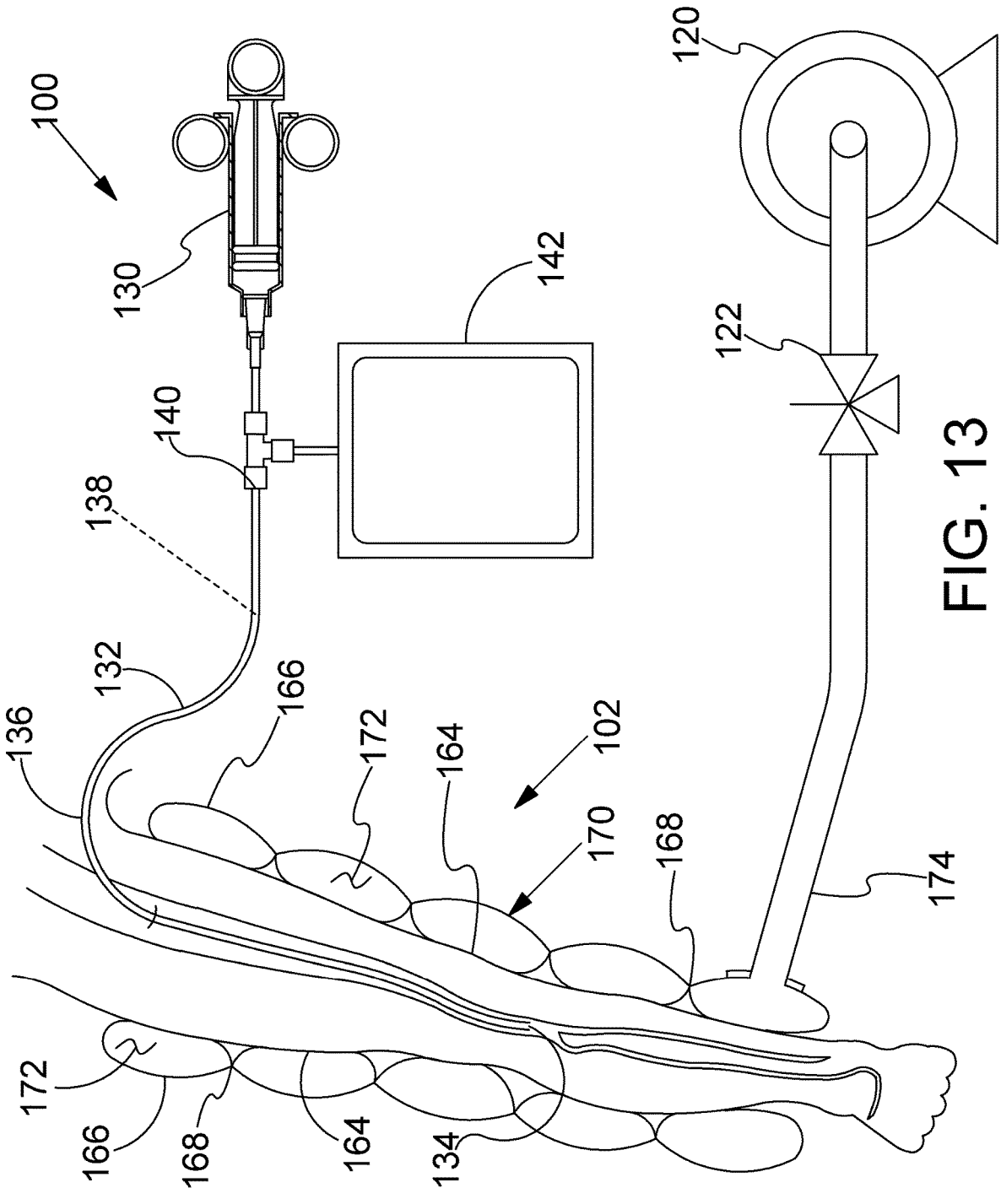

FIG. 13 is schematic plan view showing an example system including a catheter, a covering (in cross-section), and a pump.

Figure 14:
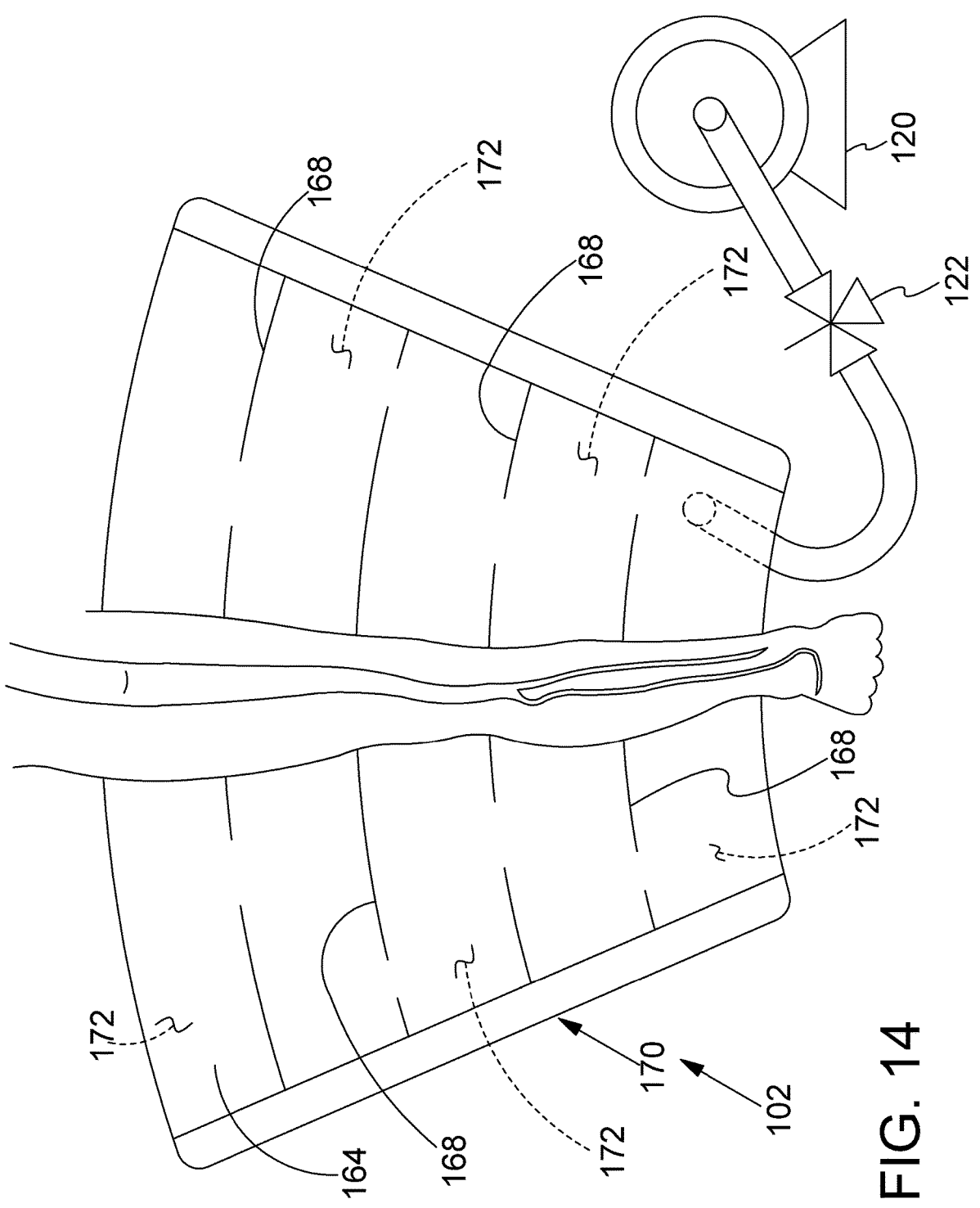

FIG. 14 is a plan view showing an example apparatus for selectively applying positive pressure to the body of a patient.

Figure 15:
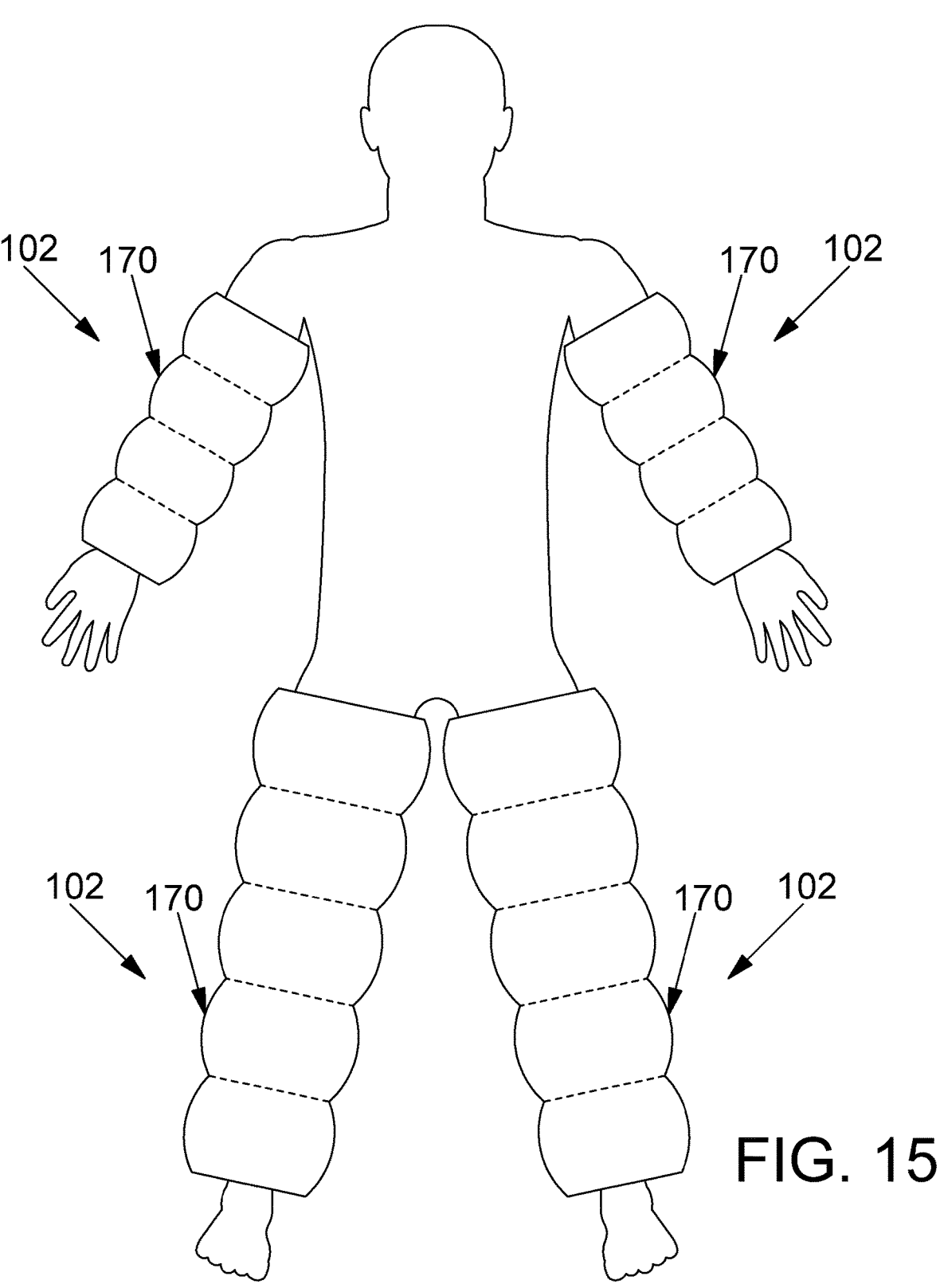

FIG. 15 is a schematic diagram showing multiple coverings on a patient.

While embodiments of the disclosure are amenable to various modifications and alternative forms, specifics thereof have been shown by way of example in the drawings and will be described in some detail. It should be understood, however, that the intention is not to limit the disclosure to the particular embodiments described. On the contrary, the intention is to cover all modifications, equivalents, and alternatives falling within the spirit and scope of the invention.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." In addition, the terms "first," "second," and the like, herein do not denote any order, quantity, or importance, but rather are used to distinguish an element or a structure from another. Moreover, the terms "a" and "an" herein do not denote a limitation of quantity, but rather denote the presence of one or more of the referenced items.

The term "distal end," or any variation thereof, refers to the portion of a device farthest from an operator of the device during a procedure. Conversely, the term "proximal end," or any variation thereof, refers to the portion of the device closest to the operator of the device. Further, any use of the terms "around," "about," "substantially," and "approximately" generally mean +/−10% of the indicated value.

DETAILED DESCRIPTION

FIG. 1A is a schematic anterior view illustrating a patient body having a vascular system. The vascular system of FIG. 1A includes a heart that pumps blood and an arterial system that distributes oxygen rich blood throughout the body. During each heartbeat, the left ventricle of the heart contracts, pumping blood through the aortic valve and into the ascending aorta. Blood from the ascending aorta flows through the aortic arch and down the descending aorta to the arteries of the lower body, returning to the heart via veins. FIG. 1B is a schematic cross-sectional perspective view showing a blood clot in a peripheral vein. A condition known as deep vein thrombosis (DVT) may occur when blood clots and/or thrombus form in the blood veins of the legs. If DVT is left untreated, blood clots can break free and travel through the bloodstream toward the heart. These blood clots can lodge in the blood vessels of a lung, blocking blood flow and causing a pulmonary embolism. FIG. 1C is a schematic cross-sectional perspective view showing a blood clot and/or thrombus located in a cerebral blood vessel which can cause a stroke. Blood clots can be removed from the body by suction, often called aspiration or thrombectomy.

FIG. 2 is a schematic cross-sectional view showing a covering or chamber 102 disposed about the body of a patient. In the example embodiment of FIG. 2, the covering 102 defines a cavity that is dimensioned and configured to receive the body of a patient. An interstitial space 104 formed between the patient body and the covering 102 can be seen in FIG. 2.

FIG. 3 is schematic plan view showing an example system 100 including a catheter 132, the covering 102 shown in FIG. 2, and a pump 120. The catheter 132 can be seen extending through an access port 188 of the covering 102. In the example embodiment of FIG. 3, the covering 102 defines a patient cavity 144 that is dimensioned and configured to receive the body of the patient. The system 100 of FIG. 3 may be used for selectively applying positive pressure to external surfaces of the body of a patient (i.e., extracorporeal positive pressure). The application of extracorporeal positive pressure may be used to improve suction in catheter 132. In general, positive pressure outside the body may be increased such that the potential negative pressure inside the body may be increased. A method for removing material from a blood vessel or cavity of a patient body may include positioning a covering to encircle at least a selected portion of the patient body so that a pressurized interstitial space 104 (see also, FIG. 2) is formed between the patient body and the covering 102. A distal opening 134 of a catheter 132 may be positioned near the material to be removed via suction.

In the example embodiment of FIG. 3, the catheter 132 includes a catheter shaft 136 defining a catheter lumen 138 having a proximal opening 140. Some example methods may include placing the proximal opening 140 of the catheter lumen 138 in fluid communication with a negative pressure source 130 so that negative pressure (suction) is applied at the target location near the distal opening 134 of the catheter 132. Material removed from a blood vessel or cavity of the patient body may be collected in a reservoir 142 in some example embodiments. In some example methods, positive pressure is applied to exterior surfaces of the patient body while (concurrently) negative pressure is applied at the target location near the distal opening 134 of the catheter 132.

The example system 100 shown in FIG. 3 includes a positive pressure source 120 and a valve mechanism 122. The valve mechanism 122 is operatively coupled between the patient cavity 144 defined by the covering 102 and the positive pressure source 120 in the example embodiment of FIG. 3. In some embodiments, the valve mechanism 122 may operate to selectively place the patient cavity 144 in fluid communication with the positive pressure source 120 (e.g., pump or compressor) so that positive pressure is applied to the body of the patient. The valve mechanism 122 may operate to selectively vent the patient cavity 144 so that atmospheric (ambient) pressure is applied to the body of the patient in some embodiments. In some embodiments, the valve mechanism 122 may operate to selectively place the patient cavity 144 in fluid communication with the ambient atmosphere so that atmospheric pressure is applied to the body of the patient.

FIG. 4 is schematic plan view showing an example system 100 including a catheter 132, a covering 102 (shown in cross-section), and a pump 120. In example embodiment of FIG. 4, the covering 102 defines a cavity that dimensioned and configured to receive a leg of a patient's body. By way of example and not limitation, the system 100 shown in FIG. 4 may be used to treat peripheral artery disease (PAD) and/or deep vein thrombosis (DVT). DVT occurs when a blood clot (thrombus) forms in one or more blood vessels (e.g., blood veins in the legs). If DVT is left untreated, blood clots can break free and travel through the bloodstream toward the heart. These blood clots can lodge in the blood vessels of a lung, blocking blood flow and causing a pulmonary embolism. Example methods and apparatus described in this document may be used to treat pulmonary embolism by aspirating blood clots lodged in the lungs. Example methods and apparatus described in this document may also be used to treat DVT by aspirating blood clots in the legs of a patient body. Removing blood clots from the legs may reduce the likelihood that pulmonary embolism will occur.

In FIG. 4, a patient's leg is shown extending into a cavity defined by the covering 102. An interstitial space 104 formed between the patient leg and the covering 102 can be seen in FIG. 4. The covering 102 may cooperate with a positive pressure source 120 and a valve mechanism 122 to apply positive pressure to the patient's leg. With reference to FIG. 4, it will be appreciated that the valve mechanism 122 is operatively coupled between the interstitial space 104 and the positive pressure source 120. In some example embodiments, the valve mechanism 122 may operate to selectively place the interstitial space 104 in fluid communication with the positive pressure source 120 so that positive pressure is applied to the body of the patient. In some embodiments, the valve mechanism 122 may operate to selectively vent the interstitial space 104 so that atmospheric (ambient) pressure is applied to the body of the patient. In some embodiments, the valve mechanism 122 may operate to selectively place the interstitial space 104 in fluid communication with the ambient atmosphere so that atmospheric pressure is applied to the body of the patient.

The catheter 132 of system 100 can be seen extending into a blood vessel of the patient's leg in FIG. 4. In the example embodiment of FIG. 4, the catheter 132 includes a catheter shaft 136 defining a catheter lumen 138 having a proximal opening 140. Example methods for removing obstructive material from a blood vessel or cavity of a patient body may include positioning the distal opening 134 of a catheter 132 near a target location inside the patient's body. Example methods for removing obstructive material from a blood vessel or cavity of a patient body may also include positioning a covering to encircle at least a selected portion of the patient body.

The proximal opening 140 of the catheter lumen 138 may be placed in fluid communication with a negative pressure source 130 so that negative pressure is applied at the target location near the distal opening 134 of the catheter 132. In some example methods, positive pressure is applied to exterior surfaces of the patient body while that negative pressure is applied at the target location near the distal opening 134 of the catheter 132. Obstructive material removed from a blood vessel or cavity of the patient body may be collected in a reservoir 142 in some example embodiments.

FIG. 5 is a perspective view showing an example apparatus for selectively applying positive pressure to the body of a patient, such as the upper torso and head. In the example embodiment of FIG. 5, the apparatus comprises a covering 102 configured to enclose a portion of the body of the patient. In the example embodiment of FIG. 5, the covering 102 comprises a headpiece portion 106 and a shoulder portion 108. The headpiece portion 106 defines a head cavity 110 and the shoulder portion 108 defines a shoulder channel 112 that fluidly communicates with the head cavity 110 in the example embodiment of FIG. 5.

Referring to FIG. 5 and FIG. 10 a superior direction Z and an inferior direction –Z are illustrated using arrows labeled "Z" and "–Z," respectively. An anterior direction Y and a posterior direction –Y are illustrated using arrows labeled "Y" and "–Y," respectively. A first lateral direction X and a second lateral direction –X are illustrated using arrows labeled "X" and "–X," respectively. The directions illustrated using these arrows are applicable to the apparatus shown and discussed throughout this application. The second lateral direction may also be referred to as a leftward direction. The first lateral direction may also be referred to as a rightward direction. In one or more embodiments, the superior direction is generally opposite the inferior direction. In one or more embodiments, the superior direction and the inferior direction are both generally orthogonal to an XY plane defined by the forward direction and the first lateral direction. In one or more embodiments, the forward direction is generally opposite the rearward direction. In one or more embodiments, the forward direction and the rearward direction are both generally orthogonal to a ZX plane defined by the superior direction and the first lateral direction. In one or more embodiments, the first lateral direction is generally opposite the second lateral direction. In one or more embodiments, first lateral direction and the second lateral direction are both generally orthogonal to a ZY plane defined by the superior direction and the forward direction. Various direction-indicating terms are used herein as a convenient way to discuss the objects shown in the figures. It will be appreciated that many direction indicating terms are related to the instant orientation of the object being described. It will also be appreciated that the objects described herein may assume various orientations without deviating from the spirit and scope of this detailed description. Accordingly, direction-indicating terms such as "upwardly," "downwardly," "forwardly," "backwardly," and the like should not be interpreted to limit the scope of the invention recited in the attached claims.

FIG. 6 is an anterior plan view of the covering 100 shown in FIG. 5. In the example embodiment of FIG. 6, the apparatus comprises a covering 102 configured to enclose a portion of the body of the patient. In the example embodiment of FIG. 6, the covering 102 comprises a headpiece portion 106 and a shoulder portion 108. The headpiece portion 106 defines a head cavity 110 and the shoulder portion 108 defines a shoulder channel 112 that fluidly communicates with the head cavity 110 in the example embodiment of FIG. 6.

Referring to FIG. 5 and FIG. 6, the covering 102 includes a chest portion 146 defining a cavity that is dimensioned and configured to receive the patient's upper torso and/or chest. A chest sealing member 114 is fixed to the chest portion 146 of the covering 102. The chest sealing member 114 defines a chest aperture 124 that fluidly communicates with the cavity defined by the chest portion 146 of the covering 102.

The chest sealing member 114 may be located and dimensioned to encircle the rib cage of the patient while the patient is wearing the covering 102.

Referring to FIG. 5 and FIG. 6, the covering 102 includes a right sleeve portion 190 that may be disposed about an upper portion of the patient's right arm and a left sleeve portion 192 that may be disposed about an upper portion of the patient's left arm. A right arm sealing member 116 is fixed to the right sleeve portion 190 of the covering 102. The right arm sealing member 116 defines a right arm aperture 118 that fluidly communicates with the shoulder channel 112 defined by the shoulder portion 108 of the covering 102. In the example embodiment shown in FIG. 5 and FIG. 6, a left arm sealing member 126 is fixed to the left sleeve portion 192 of the covering 102. The left arm sealing member 126 defines a left arm aperture 128 that fluidly communicates with the shoulder channel 112 defined by the shoulder portion 108 of the covering 102.

Referring to FIG. 5 and FIG. 6, the right arm sealing member 116 may be located and dimensioned to encircle the right arm of the patient while the patient is wearing the covering 102. The left arm sealing member 126 may be located and dimensioned to encircle the left arm of the patient while the patient is wearing the covering 102. The chest sealing member 114 may be located and dimensioned to encircle the rib cage of the patient while the patient is wearing the covering 102. In some example embodiments, each sealing member is dimensioned to engage the patient body so that a sealed interstitial space is formed between the patient body and the covering 102.

FIG. 7 is schematic plan view showing an example system 100 including a catheter 132 and the covering 102 shown in FIG. 6. The catheter 132 of system 100 can be seen extending through an incision in a femoral artery of the patient body in FIG. 7. Example methods may include inserting the distal end of catheter through an incision in the femoral artery and advancing the catheter within the vasculature system until the distal end of the catheter is located near a target location in the cerebral vasculature of the patient. In the example embodiment of FIG. 7, a portion of the patient's body is positioned inside the covering 102. The system 100 of FIG. 7 may be used for selectively applying positive pressure to external surfaces of the body of a patient and for removing occlusive material thrombus from blood vessels in the cerebral vasculature of the patient.

In some embodiments, a method for removing obstructive material from a blood vessel or cavity of a patient body may include positioning a covering to encircle at least a selected portion of the patient body so that an interstitial space 104 formed between the patient body and the covering 102. The distal opening 134 of a catheter 132 may be positioned near a target location inside the patent body (e.g., a target location in the cerebral vasculature). In some example methods, positive pressure is applied to exterior surfaces of the patient body while that negative pressure is applied at the target location near the distal opening 134 of the catheter 132. In the example embodiment of FIG. 7, the catheter 132 includes a catheter shaft 136 defining a catheter lumen 138 having a proximal opening 140. In some embodiments, the method includes placing the proximal opening 140 of the catheter lumen 138 in fluid communication with a negative pressure source 130 so that negative pressure is applied at the target location near the distal opening 134 of the catheter 132. Obstructive material removed from a blood vessel or cavity of the patient body may be collected in a reservoir 142 in some example embodiments.

The example system 100 shown in FIG. 7 includes a positive pressure source 120 and a valve mechanism 122. The valve mechanism 122 is operatively coupled between the interstitial space defined by the covering 102 and the positive pressure source 120 in the example embodiment of FIG. 7. In some embodiments, the valve mechanism 122 may operate to selectively place the interstitial space defined by the covering in fluid communication with the positive pressure source 120 so that positive pressure is applied to the body of the patient. The valve mechanism 122 may operate to selectively vent the interstitial space defined by the covering so that atmospheric pressure is applied to the body of the patient in some embodiments. In some embodiments, the valve mechanism 122 may operate to selectively place the interstitial space defined by the covering in fluid communication with the ambient atmosphere so that atmospheric pressure is applied to the body of the patient.

FIG. 8A is a cross-sectional view showing an example sealing member 150 in accordance with the present detailed description. In the example embodiment of FIG. 8A, the sealing member 150 comprises a first strip member 152 and a second strip member 154. In the embodiment of FIG. 8A, first strip member 152 is fixed second strip member 154 at an interface 158. Various methods may be used to form the interface 158 without deviating from the spirit and scope of this disclosure. Examples of methods that may be suitable in some applications include thermal welding, ultrasonic welding and fixing with adhesives. The first strip member 152 and second strip member 154 define a seal lumen 156 that is filled with a fluid 160. Fluid 160 may comprise various liquids and gases without deviating from the spirit and scope of the present description. Examples of liquids that may be suitable in some applications include water, saline, and oil. Examples of gases that may be suitable in some applications include nitrogen and air.

FIG. 8B is a plan view of sealing member 150 shown in FIG. 8A. With reference to FIG. 8B it will be appreciated that sealing member 150 includes a fill tube 162. In the embodiment of FIG. 8B, fill tube 162 extends between first strip member 152 and second strip member 154. A distal inlet of the fill tube 162 fluidly communicates with the seal lumen 156 of the sealing member 150 in the embodiment of FIG. 8B. For purposes of illustration sealing member 150 has been laid flat so that sealing member 150 has a generally planar, rectangular shape. It will be appreciated however, that the ends of sealing member 150 may be joined so that sealing member 150 forms a ring.

Various fabrication techniques may be used to fabricate sealing member 150. For example, sealing member 150 can be fabricated by providing one or more sheets of material and forming one or more interfaces 158 between opposing sheets of material. By way of a second example, sealing member 150 may be fabricated by extruding a molten material to form a tubular shaped strip. It will be appreciated that sealing members in accordance with the present detailed description can have various shapes without deviating from the spirit and scope of this description. Examples of shapes that may be suitable in some applications include cylindrical, ring-shaped, spherical, toroidal, cupped, and chevron shaped.

The first strip member 152 and the second strip member 154 may comprise various materials without deviating from the spirit and scope of the present disclosure. Examples of materials which may be suitable in some applications include polyethylene (PE), polypropylene (PP), polyvinyl-chloride (PVC), polyurethane, polytetrafluoroethylene (PTFE), and polyether block amide (PEBA). In some useful embodiments, the first strip member 152 and the second strip member 154 comprise one or more elastomeric materials. The term elastomeric generally refers to a rubber like material (e.g., a material which can experience about a 7% stretch and return to the undeformed configuration). Examples of elastomeric materials that may be suitable in some applications includes silicone rubber, polyurethane rubber, and neoprene rubber.

FIG. 9A is a perspective view of a sealing member 150 in accordance with another example embodiment. With reference to FIG. 9A it will be appreciated that sealing member 150 includes a fill tube 162. In the embodiment of FIG. 9A, fill tube 162 extends between a first strip member 152 and a second strip member 154. A distal inlet of the fill tube 162 fluidly communicates with a seal lumen 156 of the sealing member 150 in the embodiment of FIG. 9A. With reference to FIG. 9A, it will be appreciated that strip member 154 defines a generally circular aperture.

With reference to FIGS. 4-7, a covering 102 may include multiple sealing members configured as shown using the example sealing member 150 of FIG. 9A. Examples of such sealing members include chest sealing member 114, right arm sealing member 116 and left arm sealing member 126. With reference to FIG. 5, the left arm sealing member 126 may define a left arm aperture 128. With reference to FIG. 4, the sealing member 150 may define an aperture that allows a leg to extend into a covering 102.

FIG. 9B is a cross-sectional view created by the hypothetical cutting of sealing member 150 along section B-B shown in FIG. 9A. In the example embodiment of FIG. 9B, the sealing member 150 comprises a first strip member 152 and a second strip member 154. In the embodiment of FIG. 9B, first strip member 152 is fixed second strip member 154 at an interface 158. Various methods may be used to form the interface 158 without deviating from the spirit and scope of this disclosure. Examples of methods that may be suitable in some applications include thermal welding, ultrasonic welding and fixing with adhesives. The first strip member 152 and second strip member 154 define a seal lumen 156 that is filled with a fluid 160. Fluid 160 may comprise various liquids and gases without deviating from the spirit and scope of the present description.

FIG. 10A is a perspective view showing an example covering 102. FIG. 10B through FIG. 10D are elevation and plan views showing three sides of the covering 102 shown in the perspective view of FIG. 10A. Engineer graphics textbooks generally refer to the process used to create views showing six sides of a three-dimensional object as multiview projection or orthographic projection. It is customary in the field of engineering graphics to refer to multiview projections using terms such as front view, side view, top view, rear view, and bottom view. In accordance with this convention, FIG. 10B may be referred to as a front view of the covering, FIG. 10C may be referred to as a side view of the covering, and FIG. 10D may be referred to as a cross-sectional top view of the covering. FIG. 10A through FIG. 10C may be referred to collectively as FIG. 10. Terms such as front view and top view are used herein as a convenient method for differentiating between the views shown in FIG. 10. It will be appreciated that the elements shown in FIG. 10 may assume various orientations without deviating from the spirit and scope of this detailed description. Accordingly, terms such as front view, side view, top view, and the like should not be interpreted to limit the scope of the invention recited in the attached claims.

In the example embodiment of FIG. 10, the covering 102 comprises a plurality of wall portions defining a patient cavity 144. In the example embodiment of FIG. 10, the plurality of wall portions include an anterior wall portion 176, a posterior wall portion 178, a right wall portion 180, a left wall portion 182, a superior wall portion 184, and an inferior wall portion 186. In the example embodiment of FIG. 10, the anterior wall portion 176 of the covering 102 extends in the leftward direction –X from the right wall portion 180 to the left wall portion 182 and extends in the rightward direction X from the left wall portion 182 to the right wall portion 180. The anterior wall portion 176 also extends in the superior direction from the inferior wall portion 186 to the superior wall portion 184 and extends in the inferior direction –Z from the superior wall portion 184 to the inferior wall portion 186 in the embodiment of FIG. 10.

In the example embodiment of FIG. 10, the right wall portion 180 extends in the anterior direction –Y from the posterior wall portion 178 to the anterior wall portion 176 and extends in the posterior direction from the anterior wall portion 176 to the posterior wall portion 178. The right wall portion 180 also extend in the superior direction from the inferior wall portion 186 to the superior wall portion 184 and extends in the inferior direction –Z from the superior wall portion 184 to the inferior wall portion 186 in the embodiment of FIG. 10. In the example embodiment of FIG. 10, the inferior wall portion 186 of the covering 102 extends in the leftward direction –X from the right wall portion 180 to the left wall portion 182 and extends in a rightward direction X from the left wall portion 182 to the right wall portion 180. The inferior wall portion 186 also extends in the anterior direction –Y from the posterior wall portion 178 to the anterior wall portion 176 and extends in the posterior direction from the anterior wall portion 176 to the posterior wall portion 178 in the embodiment of FIG. 10.

In the example embodiment of FIG. 10, the posterior wall portion 178 of the covering 102 extends in the leftward direction –X from the right wall portion 180 to the left wall portion 182 and extends in the rightward direction X from the left wall portion 182 to the right wall portion 180. The posterior wall portion 178 also extends in the superior direction from the inferior wall portion 186 to the superior wall portion 184 and may extend in the inferior direction –Z from the superior wall portion 184 to the inferior wall portion 186 in the example embodiment of FIG. 10. In the example embodiment of FIG. 10, the left wall portion 182 extends in the anterior direction –Y from the posterior wall portion 178 to the anterior wall portion 176 and extends in the posterior direction from the anterior wall portion 176 to the posterior wall portion 178. The left wall portion 182 also extends in the superior direction from the inferior wall portion 186 to the superior wall portion 184 and may extend in the inferior direction –Z from the superior wall portion 184 to the inferior wall portion 186 in the embodiment of FIG. 10. In the example embodiment of FIG. 10, the superior wall portion 184 of the covering 102 extends in the leftward direction –X from the right wall portion 180 to the left wall portion 182 and extends in the rightward direction X from the left wall portion 182 to the right wall portion 180. The superior wall portion 184 also extends in the anterior direction –Y from the posterior wall portion 178 to the anterior wall portion 176 and extends in the posterior direction from the anterior wall portion 176 to the posterior wall portion 178 in the embodiment of FIG. 10.

FIG. 11 is schematic plan view showing an example system 100 including a catheter 132 and the covering 102 shown in FIG. 10. The catheter 132 is shown extending through an access port 188 of the covering 102 in FIG. 11.

In the example embodiment of FIG. 11, the covering 102 defines a patient cavity 144 that is dimensioned and configured to receive the body of the patient. The system 100 of FIG. 11 may be used for selectively applying positive pressure to external surfaces of the body of a patient and/or for removing obstructions and/or thrombus from blood vessels. The example system 100 shown in FIG. 11 includes a positive pressure source 120 operatively coupled to the patient cavity 144 through a valve mechanism 122. In some embodiments, the valve mechanism 122 may operate to selectively place the patient cavity 144 in fluid communication with the positive pressure source 120 so that positive pressure is applied to the body of the patient. The valve mechanism 122 may operate to selectively vent the patient cavity 144 so that atmospheric pressure is applied to the body of the patient in some embodiments. In some embodiments, the valve mechanism 122 may operate to selectively place the place patient cavity 144 in fluid communication with the ambient atmosphere so that atmospheric pressure is applied to the body of the patient. In the example embodiment of FIG. 11, the catheter 132 of system 100 a catheter shaft 136 that defines a catheter lumen 138 extending between a distal opening 134 and a proximal opening 140. Example system 100 also includes a negative pressure source 130 that may selectively apply negative pressure to the proximal opening 140 of the catheter lumen 138 so that negative pressure is applied at the target location near the distal opening 134 of the catheter 132.

FIG. 12 is a cross-sectional view showing an example system 100 for selectively applying positive pressure to the body of a patient. The example system 100 of FIG. 12 comprises a covering 102, a positive pressure source 120 and a valve mechanism 122. The covering 102 of system 100 comprises an inflatable sleeve 170 that is dimensioned and configured to wrap around a portion of the body of the patient. In the example embodiment of FIG. 12, the inflatable sleeve 170 comprises a first sheet 164 and a second sheet 166. The first sheet 164 is fixed second sheet 166 at a plurality of weld lines 168 in the embodiment of FIG. 12. Various methods may be used to form the plurality of weld lines 168 without deviating from the spirit and scope of this disclosure. Examples of methods that may be suitable in some applications include thermal welding, ultrasonic welding and fixing with adhesives.

With reference to FIG. 12, it will be appreciated that the weld lines 168 between the first sheet 164 and second sheet 166 help to define a plurality of inflation chambers 172 that are filled with a fluid 160. The fluid 160 may comprise various liquids and gases without deviating from the spirit and scope of the present description. Examples of liquids that may be suitable in some applications include water, saline, and oil. Examples of gases that may be suitable in some applications include nitrogen and air.

In some embodiments, the covering 102 of system 100 may cooperate with the positive pressure source 120 and the valve mechanism 122 to apply positive pressure to the leg of a patient. In the example embodiment of FIG. 12, the valve mechanism 122 is operatively coupled between the inflation chambers 172 of the inflatable sleeve 170 and the positive pressure source 120. The valve mechanism 122 may operate to selectively place the inflation chambers 172 in fluid communication with the positive pressure source 120 so that positive pressure enters the inflation chambers 172 and the inflation chambers apply positive pressure to the body of the patient.

FIG. 13 is schematic plan view showing an example system 100 including a catheter 132 and a covering 102 that is illustrated using a cross-sectional view. In example embodiment of FIG. 13, the covering 102 comprises an inflatable sleeve 170 that is disposed about the leg of a patient. The inflatable sleeve 170 may cooperate with a positive pressure source 120 and a valve mechanism 122 to apply positive pressure to the patient leg. In the example embodiment of FIG. 13, the valve mechanism 122 is operatively coupled between the inflation chambers 172 of the inflatable sleeve 170 and the positive pressure source 120. The valve mechanism 122 may operate to selectively place the inflation chambers 172 in fluid communication with the positive pressure source 120 so that positive pressure enters the inflation chambers 172 and the inflation chambers apply positive pressure to the body of the patient.

The catheter 132 of system 100 can be seen extending into a blood vessel of the patient's leg in FIG. 13. In the example embodiment of FIG. 13, the catheter 132 includes a catheter shaft 136 defining a catheter lumen 138 having a proximal opening 140. Example methods for removing obstructive material from a blood vessel or cavity of a patient body may include positioning the distal opening 134 of a catheter 132 near a target location inside the patient's body. Example methods for removing obstructive material from a blood vessel or cavity of a patient body may also include positioning an inflatable sleeve (e.g., inflatable sleeve 170) to encircle at least a selected portion of the patient body. The proximal opening 140 of the catheter lumen 138 may be placed in fluid communication with a negative pressure source 130 so that negative pressure is applied at the target location near the distal opening 134 of the catheter 132. In some example methods, positive pressure is applied to exterior surfaces of the patient body while that negative pressure is applied at the target location near the distal opening 134 of the catheter 132. Obstructive material removed from a blood vessel or cavity of the patient body may be collected in a reservoir 142 in some example embodiments.

In the example embodiment of FIG. 13, the inflatable sleeve 170 comprises a first sheet 164 and a second sheet 166. The first sheet 164 is fixed second sheet 166 at a plurality of weld lines 168 in the embodiment of FIG. 13. With reference to FIG. 13, it will be appreciated that the weld lines 168 between the first sheet 164 and second sheet 166 help to define a plurality of inflation chambers 172. The inflation chambers 172 may be selectively placed in fluid communication with positive pressure source 120 via valve mechanism 122. The first sheet 164 and the second sheet 166 may comprise various materials without deviating from the spirit and scope of the present disclosure. Examples of materials which may be suitable in some applications include polyethylene (PE), polypropylene (PP), polyvinyl-chloride (PVC), polyurethane, polytetrafluoroethylene (PTFE), and polyether block amide (PEBA). In some useful embodiments, the first sheet 164 and the second sheet 166 comprise one or more elastomeric materials. The term elastomeric generally refers to a rubber like material (e.g., a material which can experience about a 7% stretch and return to the undeformed configuration). Examples of elastomeric materials that may be suitable in some applications includes silicone rubber, polyurethane rubber, and neoprene rubber.

FIG. 14 is a plan view showing an example apparatus for selectively applying positive pressure to the body of a patient. In the example embodiment of FIG. 14, the apparatus includes a covering 102 comprising an inflatable sleeve 170 that is configured to be disposed about the leg of a patient. In the example embodiment of FIG. 14, the inflatable sleeve 170 comprises a first sheet 164 that is overlaying a second sheet. The first sheet 164 is fixed second sheet at a plurality of weld lines 168 in the embodiment of FIG. 14. Various methods may be used to form the plurality of weld lines 168 without deviating from the spirit and scope of this disclosure. With reference to FIG. 14, it will be appreciated that the weld lines 168 between the first sheet 164 and second sheet define a plurality of inflation chambers 172 that may be selectively filled with fluid (e.g., liquid or gas). The covering 102 of system 100 may cooperate with the positive pressure source 120 and the valve mechanism 122 to apply positive pressure to the leg of a patient. In the example embodiment of FIG. 14, the valve mechanism 122 is operatively coupled between the inflation chambers 172 of the inflatable sleeve 170 and the positive pressure source 120. The valve mechanism 122 may operate to selectively place the inflation chambers 172 in fluid communication with the positive pressure source 120 so that positive pressure enters the inflation chambers 172 and the inflation chambers apply positive pressure to the body of the patient.

FIG. 15 is a schematic diagram showing a patient and four coverings. In the example embodiment of FIG. 15, each covering 102 comprises an inflatable sleeve 170 that is dimensioned and configured to wrap around a portion of the body of the patient. One inflatable sleeve 170 is wrapped around each of the patient's legs in the example embodiment of FIG. 15. One inflatable sleeve 170 is also wrapped around each of the patient's arms in the example embodiment of FIG. 15.

Referring to FIGS. 1 through 15, a method for removing obstructive material from a blood vessel or cavity of a body may comprise positioning a covering to enclose at least a portion of the body. In some example methods, an interior space defined by the covering is placed in fluid communication with a positive pressure source so that positive pressure is applied to the portion of the body enclosed by the covering. In some example methods, the distal opening of a catheter is positioned near a target location inside the body and a proximal opening of the catheter is placed in fluid communication with a negative pressure source so that negative pressure is applied at the target location near the distal end of the catheter. In some embodiments, the catheter has a distal end, a proximal end, a shaft extending between the distal end and the proximal end. In some embodiments, the shaft defines a lumen having a distal opening and a proximal opening. In some example applications, the target location is located inside a cerebral vasculature of the body and/or located inside a cranial cavity of the body. In some example applications the target location is located inside a peripheral vasculature of the body and/or located inside a limb of the body (e.g., a leg). In some example methods, the positive pressure has a magnitude greater than 80 mm Hg (gauge) and less than 120 mm Hg (gauge). In some example methods, the positive pressure has a magnitude greater than 200 mm Hg (gauge) and less than 800 mm Hg (gauge). In some example methods, the negative pressure has a magnitude greater than −760 mm Hg (gauge) and less than −100 mm Hg (gauge). In some example methods, the positive pressure and the negative pressure are applied concurrently. In some example methods, the positive pressure and the negative pressure are applied at different times.

Referring to FIGS. 1 through 15, in some embodiments, a system for selectively applying positive pressure to a body of a patient comprises a covering configured to enclose a portion of the body, the covering having an inside surface defining an interior space dimensioned and configured to receive a portion of the body. The system may further include a positive pressure source and a valve mechanism operatively coupled between the interior space and the positive pressure source, the valve mechanism selectively placing the interior space in fluid communication with the positive pressure source so that positive pressure is applied to the portion of the body. In some embodiments, the covering is configured to enclose the head, torso, arms, hands, legs, and feet of the body. In some embodiments, the covering comprises a sleeve portion that is dimensioned and configured to encircle an arm of the body. In some embodiments, the covering comprises a leg portion that is dimensioned and configured to encircle a leg of the body. In some embodiments, comprises a torso portion that is dimensioned and configured to encircle a torso of the body. In some embodiments, the covering comprises a headpiece that is dimensioned and configured to encircle a head of the body. In some embodiments, the positive pressure source comprises a compressor and a reservoir. In some embodiments, the positive pressure source comprises a blower.

The following U.S. patents are hereby incorporated by reference herein: U.S. Ser. No. 10/390,849, U.S. Ser. No. 10/485,551, U.S. Ser. No. 10/485,564, U.S. Ser. No. 10/799, 244, U.S. Ser. No. 10/806,474, U.S. Ser. No. 10/863,999, U.S. Pat. Nos. 9,017,309, 8,764,724, 7,896,825, 7,736,355, 7,250,042, 7,244,250, 6,849,068, 5,938,645, 5,827,229, 5,749,858, 5,569,204, and 5,234,403. The above references to U.S. patents in all sections of this application are herein incorporated by references in their entirety for all purposes. Components illustrated in such patents may be utilized with embodiments herein. Incorporation by reference is discussed, for example, in MPEP section 2163.07(B).

All of the features disclosed in this specification (including the references incorporated by reference, including any accompanying claims, abstract and drawings), and/or all of the steps of any method or process so disclosed, may be combined in any combination, except combinations where at least some of such features and/or steps are mutually exclusive.

Each feature disclosed in this specification (including references incorporated by reference, any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any incorporated by reference references, any accompanying claims, abstract and drawings), or to any novel one, or any novel combination, of the steps of any method or process so disclosed. The above references in all sections of this application are herein incorporated by references in their entirety for all purposes.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative aspects. The above-described aspects embodiments of the invention are merely descriptive of its principles and are not to be considered limiting. Further modifications of the invention herein disclosed will occur to those skilled in the respective arts and all such modifications are deemed to be within the scope of the invention.

What is claimed is:

1. A method of removing material from a blood vessel or cavity inside a body, the method comprising:

inserting a catheter into the blood vessel or cavity, the catheter having an elongate shaft, a proximal portion, a distal portion and a lumen extending therethrough to a distal opening;

positioning the distal opening of the catheter in the blood vessel or cavity proximate the material to be removed;

applying extracorporeal positive pressure to at least a portion of the body containing the material to be removed;

applying suction to the proximal portion of the catheter while the extracorporeal positive pressure is being applied; and wherein the extracorporeal positive pressure is applied by a pressure chamber surrounding the entire body.

2. The method as in claim 1, wherein the extracorporeal positive pressure is applied at a location that surrounds the portion of the body containing the material to be removed.

3. The method as in claim 1, wherein the extracorporeal positive pressure is applied at locations that are proximal and distal of the portion of the body containing the material to be removed.

4. The method as in claim 1, wherein the suction is applied before applying the extracorporeal positive pressure, and wherein the suction continues while the extracorporeal positive pressure is being applied.

5. The method as in claim 1, wherein the catheter is inserted into the body at an access site, and wherein the access site is proximal of the portion of the body where extracorporeal pressure is applied.

6. A method of removing material from a blood vessel or cavity inside a body, the method comprising:

inserting a catheter into the blood vessel or cavity, the catheter having an elongate shaft, a proximal portion, a distal portion and a lumen extending therethrough to a distal opening;

positioning the distal opening of the catheter in the blood vessel or cavity proximate the material to be removed;

applying extracorporeal positive pressure to at least a portion of the body containing the material to be removed; and applying suction to the proximal portion of the catheter while the extracorporeal positive pressure is being applied;

wherein the extracorporeal positive pressure is applied by a compression device;

wherein the compression device applies dynamic pressure; and wherein the dynamic pressure is applied progressively in a distal to proximal direction.

7. The method of claim 6, wherein the compression device comprises an inflatable table device.

8. The method of claim 6, wherein the compression device is an elastic device.

* * * * *